(12) United States Patent
Flugelman et al.

(10) Patent No.: US 7,524,493 B2
(45) Date of Patent: Apr. 28, 2009

(54) NUCLEIC ACID CONSTRUCTS CELLS TRANSFORMED THEREWITH AND METHODS UTILIZING SAME FOR INDUCING LIVER REGENERATION AND ALLEVIATION OF PORTAL HYPERTENSION

(75) Inventors: Moshe Y. Flugelman, Haifa (IL); Zoya Gluzman, Tal-El (IL); Meir Preis, Haifa (IL); Belly Koren, Yokneam Ilit (IL); Tzafra Cohen, Haifa (IL); Adili Tsaba, Haifa (IL); Michael Ott, Wunstorf (DE)

(73) Assignee: M.G.V.S. Ltd., Haifa (IL)

( * ) Notice: Subject to any disclaimer, the term of this patent is extended or adjusted under 35 U.S.C. 154(b) by 628 days.

(21) Appl. No.: 10/468,404

(22) PCT Filed: Feb. 28, 2002

(86) PCT No.: PCT/IL02/00153

§ 371 (c)(1),
(2), (4) Date: Sep. 2, 2003

(87) PCT Pub. No.: WO02/070019

PCT Pub. Date: Sep. 12, 2002

(65) Prior Publication Data

US 2004/0116343 A1    Jun. 17, 2004

Related U.S. Application Data

(63) Continuation-in-part of application No. 09/796,543, filed on Mar. 2, 2001, now abandoned.

(51) Int. Cl.
*A61K 48/00* (2006.01)
*C12N 5/10* (2006.01)
*C07H 21/04* (2006.01)
*C12N 15/85* (2006.01)

(52) U.S. Cl. ............ 424/93.3; 424/93.1; 424/93.2; 424/93.21; 435/325; 435/363; 435/370; 435/371

(58) Field of Classification Search ................. None
See application file for complete search history.

(56) References Cited

U.S. PATENT DOCUMENTS 5,654,404 A * 8/1997 Roos et al. ............... 530/387.3

FOREIGN PATENT DOCUMENTS

| EP | 1132098 | 9/2001 |
|---|---|---|
| WO | WO 94/06456 | 3/1994 |
| WO | WO 02/02148 | * 1/2002 |

OTHER PUBLICATIONS

Li et al. (2000) J Thorac. Cardiovasc. Surg. 119:62-68.*
Srour et al. (1999) J. Hematother. 8:93-102.*
Gage Nature (1998) 392:18-24.*
Jain et al. (2000) Nat. Med. 6: 131-132.*
de Silva et al. (2004) Cytotherapy 6:608-614.*
Parikh et al. (2000) Adv Drug Deliv Rev. 42:139-61.*
Samstein et al. (2001) J. Am. Soc. Nephrol. 12: 182-193.*
Eck et al. (1996) Goodman & Gilman's The Pharmacological Basis of Therapeutics, 9th Edition, Chapter 5, McGraw-Hill, NY.*
Rubanyi (2001) Mol. Aspects Med. 22:113-142.*
Ross et al. Human gene Therapy, vol. 7, pp. 1781-1790.*
Rissanen et al. (2001) Eur. J. Clin. Invest. 31:651-666.*
Emanueli et al. (2001) 133 :951-958.*
Laleman et al. (2005) Liver Int. 25:1079-1090.*
Rafii et al. (2003) Nature Med. 9:702-712.*
Scheur, P.J. Section 7.1: cirrhosis and chronic active hepatitis in Oxford Textbook of Clinical Hepatology, vol. 1, (McIntyre et al., eds.) Oxford University Press, 1991.*
Rojkind et al. Section 7.2: Pathophysiology of liver fibrosis, in Oxford Textbook of Clinical Hepatology vol. 1, (McIntyre et al., eds.) Oxford University Press, 1991.*
Erlinger et al. Section 7.3: Cirrhosis: clinical aspects, in Oxford Textbook of Clinical Hepatology, vol. 1, (McIntyre et al., eds.) Oxford University Press, 1991.*
Barr et al. (1994) Gene Ther. 1:51-58.*
Phaneuf et al. (2000) Mol. Med. 6:96-103.*
Ajioka et al. (1999) Hepatol. 29:396-402.*
Kaido et al. (1996) Biochem. Biophys. Res. Commun. 218:1-5.*
Oe (2004) Hepato-Gastroenterol. 51:1641-1647.*
Medina (2003) J. Hepatol. 38:660-667.*
Phaneuf et al. "Intravenous Injection of an Adenovirus Encoding Hepatocyte Growth Factor Results in Liver Growth and has a Protective Effect Against Apoptosis", Molecular Medicine, 6(2): 96-103, 2000.
Assy et al. "Effect of Vascular Endothelial Growth Factor on Hepatic Regenerative Activity Following Partial Hepatectomy in Rats", J. Hepatol, 30(5): 911-915, 1999.
Taniguchi et al. "Expression and Role of Vascular Endothelial Growth Factor in Liver Regeneration After Partial Hepatectomy in Rats", Journal of Histochemistry and Cytochemistry, 49(1): 121-130, 2001.
Davern, T.J. II. "Gene Therapy for Liver Disease", Dig., Dis., 16: 23-37, 1998.
Fujimotot, J. "Gene Therapy for Liver Cirrhosis", J. Gastroenterol. Hepatol., 15(suppl.): D33-D36, 2000.
Peng et al. "Synergistic Enhancement of Bone Formation and Healing by Stem Cell-Expressed VEGF and Bone Morphogenetic Protein-4", J. Clin. Invest., 110(6): 751-759, Sep. 2002.
Lubiatowski et al. "Gene Therapy by Adenovirus-Mediated Vascular Endothelial Growth Factor and Angiopoietin-1 Promotes Perfusion of Muscle Flaps", Plast Reconstr. Surg., 110(1): 149-159, 2002.
Hacein-Bey-Abina et al. "Sustained Correction of X-Linked Severe Combined Immunodeficiency by Ex-Vivo Gene Therapy", N. Engl. J. Med., 346(16): 1185-1193, 2002.
Somia et al. "Gene Therapy: Trials and Tribulations", Nature Revues/ Genetics, 1(2): 91-99, 2000.
Ennis et al. "Dual Gene Therapy With SERCA1 and Kir2.1 Abbreviates Excitation Without Suppressing Contractility", J. Clin. Invest., 109(3): 393-400, 2002.

(Continued)

*Primary Examiner*—David Guzo

(57) ABSTRACT

A method of inducing liver regeneration in a damaged liver tissue region of an individual is provided. The method including the step of providing at least two distinct growth factors to the damaged liver tissue region of the individual, at least one of the at least two distinct growth factors being an angiogenic factor.

8 Claims, 19 Drawing Sheets
(12 of 19 Drawing Sheet(s) Filed in Color)

OTHER PUBLICATIONS

Orkin et al. "Report and Recommendations of the Panel to Assess the Nih Investment in Research on Gene Therapy": 1-33, 1995.

Verma et al. "Gene Therapy—Promises, Problems and Prospects", Nature, 389: 239-242, 1997.

Oren et al. "Restoration of Serum albumin Levels in Nagase Analbuminemic Rats by Hepatocyte Transplantation", Hepatology, 29(1): 75-81, 1999.

Laskus et al. "Dynamic Behavior of Hepatitis C Virus in Chronically Infected Patients Receiving Liver Graft From Infected Donors", Virology, 220(0297): 171-176, 1996.

Marshall, E. "Gene Therapy's Growing Pains", Science, 269: 1050-1055, 1995.

Hickman et al. "Gene Expression Following Direct Injection of DNA into Liver", Human Gene Therapy 5: 1477-1483, 1994.

Isner et al. "Assessment of Risks Associated With Cardiovascular Gene Therapy in Human Subjects", Circ Res. 89: 389-400, 2001.

Irani et al. "Correction of Liver Disease Following Transplantation of Normal Rat Hepatocytes into Long-Evans Cinnamon Rats Modeling Wilson's Disease", Molecular Therapy 3(3): 302-309, 2001.

Losordo et al. "Phase 1/2 Placebo-Controlled, Double-Blind, Dose-Escalating Trial of Myocardial Vascular Endothelial Growth Factor 2 Gene Tranfer by Catheter Delivery in Patients With Chronic Myocardial Ischemia", Circulation 150: 2012-2018, 2002.

Grines et al. "Angiogenic Gene Therapy (AGENT) Trial in Patients With Stable Angina Pectoris", Circulation 105: 1291-1297, 2002.

Aiuti et al. "Correction of ADA-SCID by Stem Cell Gene Therapy Combined with Nonmyeloablative Conditioning", Science 296: 2410-2413, 2002.

Rosen "Successful Gene Therapy for Severe Combined Immunodeficiency", N Engl J Med 346(16): 1241-1243, 2002.

Chae et al. "Coadministration of Angiopoietin-1 and Vascular Endothelial Growth Factor Enhances Collateral Vascularization", Arterioscler Thromb Vasc Biol. 20: 2573-2578, 2000.

Morishita "Recent Progress in Gene Therapy for Cardiovascular Disease", Circ J 66: 1077-1086, 2002.

High "Gene Therapy: a 2001 Perspective", Haemophilia 7(suppl. 1): 23-27, 2001.

Siegel "Biotechnology and Clinical Trials", The Journal of Infectious Diseases 185(suppl. 1): S52-7, 2002.

Kauczor et al. "CT-Guided Intratumoral Gene Therapy in Non-Small-Cell Lung Cancer", Eur. Radiol. 9: 292-296, 1999.

Klatzmann et al. "A Phase I/II Study of Herpes Simplex Virus Type 1 Thymidine Kinase "Suicide" Gene Therapy for Recurrent Glioblastoma", Human Gene Therapy 9: 2595-2604, 1998.

Cavazzana-Calvo et al. "Gene Therapy of Human Severe Combined Immunodeficiency (SCID)-X1 Disease", Science 288: 669-672, 2000.

Palmer et al. "Gene Therapy with Autologous, Interleukin 2-Secreting Tumor Cells in Patients with Malignant Melanoma", Human Gene Therapy 10: 1261-1268, 1999.

Herman et al. "In Situ Gene Therapy for Adenocarcinoma of the Prostate: A Phase I Clinical Trial", Human Gene Therapy 10: 1239-1249, 1999.

Isner "Myocardial Gene Therapy", Nature 415: 234-239, 2002.

Liebert "Assessment of Adenoviral Vector Safety and Toxicity: Report of the National Institutes of Health Recombinant DNA Advisory Committee", Human Gene Therapy 13: 3-13, 2002.

* cited by examiner

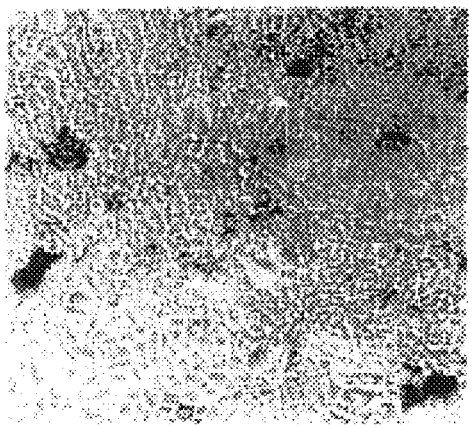
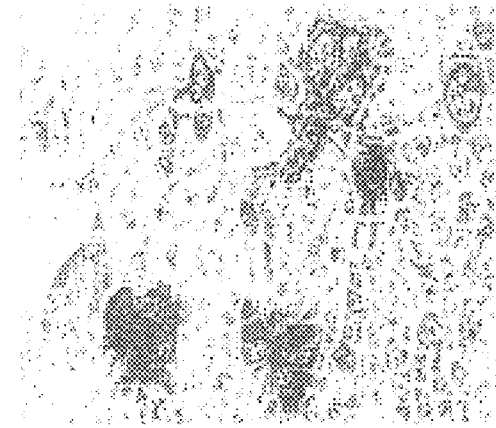
Fig. 5a          Fig. 5b
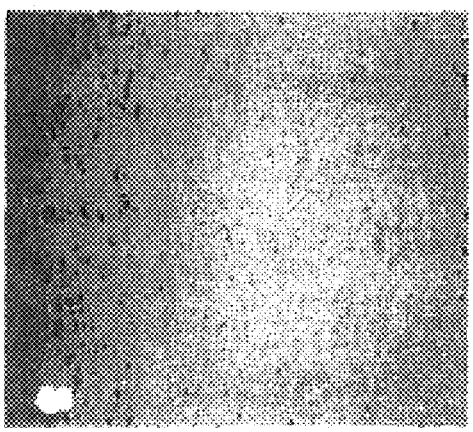
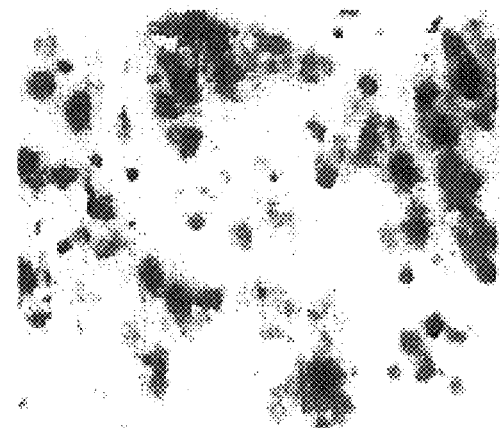
Fig. 6a          Fig. 6b

NUCLEIC ACID CONSTRUCTS CELLS TRANSFORMED THEREWITH AND METHODS UTILIZING SAME FOR INDUCING LIVER REGENERATION AND ALLEVIATION OF PORTAL HYPERTENSION

RELATED APPLICATIONS

This Application is a National Phase of PCT Patent Application No. PCT/IL02/00153 having International Filing Date of Feb. 28, 2002, which is a Continuation-in-Part of U.S. patent application Ser. No. 09/796,543 filed on Mar. 2, 2001 now abandoned.

FIELD AND BACKGROUND OF THE INVENTION

The present invention relates to nucleic acid constructs, cells transformed therewith and methods of utilizing such constructs and transformed cells for inducing hepatocytes proliferation and liver regeneration.

Liver Cirrhosis

Cirrhosis, is a disease of the liver, which results from injury to liver tissue. Cirrhosis is characterized by scar tissue formation throughout the organ; groups of cells termed regenerative nodules, surrounded by sheets of scar tissue, replace the normal tissue of the liver. The diseased organ may be unable to perform vital functions such as manufacturing proteins and removing harmful substances from the blood. The affected liver tissue may block the flow of blood through the liver, causing high pressure in blood vessels, which serve the liver (portal hypertension). This blockage can lead to gastroesophageal bleeding and ascites and in addition can contribute to the development of encephalopathy.

Liver injury occurs as a result of a number of acute and chronic clinical conditions, including drug-induced hepatotoxicity, viral infections, vascular injury, autoimmune disease, and blunt trauma. In addition, patients subject to inborn metabolic abnormalities may be at risk for developing liver cirrhosis.

Liver cirrhosis and its related clinical syndromes is a major cause of morbidity and mortality both in the developed and developing countries (Podolsky et al, 1988; Sherlock et al, 1997; Villanueva et al, 1996). According to the National Institute of Diabetes and Digestive and Kidney Diseases about 25,000 Americans die from cirrhosis each year.

Currently, liver damage resulting from cirrhosis cannot be reversed, although complications resulting from such liver damage can be treated by a variety of treatment regimens, which are targeted at preventing or alleviating such complications. For example, ascites and edema, are treatable by a low-sodium diet or use of diuretics, infections are treatable via antibiotics, while blood pressure medication (e.g., a beta-blocker) can be utilized to reduce the occurrence of gastro-intestinal bleeding in portal hypertension cases.

In extreme cases of liver dysfunction, liver transplant procedures are necessary. Although liver transplants can reestablish normal liver function such procedures are complex and as such only successful in a fraction of the cases. In addition, constant shortage of organs suitable for transplantation further limits application of this procedure.

Thus, current treatment regimens for cirrhosis-related liver damage provide solutions for some of the complications accompanying cirrhosis while being useless in inducing liver repair and regeneration.

Liver Regeneration and Angiogenesis

Liver regeneration is a dynamic process in which proliferation of cells such as hepatocytes, biliary epithelial cells, and endothelial cells occurs. Liver tissue regeneration is believed to be controlled by various growth stimulating and inhibiting factors of autocrine or paracrine origin acting in concert; however, the exact role and mechanism of these factors is yet to be understood.

Liver tissue exhibits some self-regenerative properties, which are dependent on proper function of the complex vascular structure of the liver.

It has been observed that partial hepatectomy induces proliferation of all cells populations within the liver. Such cellular proliferation initiates in the periportal region (i.e. around the portal triads) and proceeds toward the centers of lobules. Proliferating hepatocytes initially form clumps, which soon transform into classical plates. Similarly, proliferating endothelial cells develop into the type of fenestrated cells typical of the sinusoids, which carry blood within the liver.

Liver angiogenesis, which is the formation of new blood vessels in liver tissue, is controlled by cells which secrete angiogenic and angiostatic factors (Yamane et al, 1994; Monacci et al, 1993).

One such angiogenic factor is vascular endothelial growth factor (VEGF) which posses endothelial-specific mitogenic and angiogenic properties and as such plays a multi-factorial role in development and maintenance of the vascular structure. In the liver, VEGF, which is secreted in a soluble form from hepatocytes, binds the VEGF-specific endothelial receptors, flt-1 and KDR/flk1 (Monacci et al, 1993; Jakeman et al, 1992). Although three VEGF receptors are known, the KDR/flk1 is probably the receptor functional in angiogenesis (Hanahan et al, 1997).

Little is known about the molecular regulation of angiogenesis and the communication of hepatocytes and sinusoidal endothelial cells in the liver.

Following partial hepatectomy VEGF expression is increased with a maximum level at 72 hours which is followed by expression of its receptors on sinusoidal endothelial cells (maximum 72-168 hours) (Mochida et al, 1996). Plasma VEGF levels are increased in acute hepatitis and in patients recovering from fulminant hepatitis (Akiyoshi et al, 1998). In addition, VEGF increased the rate of DNA synthesis in rat liver tissue following partial hepatectomy.

Hepatocyte growth factor (HGF) is another growth stimulating factor, which participates in liver regeneration. This growth factor which contributes to maintenance and proliferation of primary liver cells is expressed in the sinusoidal endothelial cells (Noji et al, 1990). It has been observed that HGF levels increase in the plasma of patients with hepatic failure and in the plasma or serum of animals with experimentally induced liver damage. The kinetics of this response is usually rapid, and precedes the first round of DNA synthesis during liver regeneration.

While reducing the present invention to practice, the present inventors have uncovered that localized over-expression of VEGF and HGF in liver tissue can be utilized to enhance liver regeneration, capillary production, and formation of sinusoidal network.

Thus, over-expression of such growth factors in liver tissue can be used to induce liver tissue regeneration and to prevent or alleviate portal hypertension thus providing an alternative treatment strategy for a variety of untreatable liver diseases.

SUMMARY OF THE INVENTION

According to one aspect of the present invention there is provided a nucleic acid expression construct comprising: (a) a first polynucleotide segment encoding a first growth factor; and (b) a second polynucleotide segment encoding a second growth factor, at least one of the first and the second growth factors being an angiogenic factor.

According to another aspect of the present invention there is provided a nucleic acid expression construct system comprising: (a) a first nucleic acid expression construct including a first polynucleotide segment encoding first growth factor; and (b) a second nucleic acid expression construct including a second polynucleotide segment encoding a second growth factor, at least one of the first and the second growth factors being an angiogenic factor.

According to further features in preferred embodiments of the invention described below, the nucleic acid expression construct further comprising at least one promoter sequence being for directing the expression of at least one of the first and the second polynucleotide segments.

According to still further features in the described preferred embodiments the first polynucleotide segment is transcriptionally linked to the second polynucleotide segment whereas the first and the second polynucleotide segment are under the transcriptional control of a single promoter sequence of the at least one promoter sequence.

According to still further features in the described preferred embodiments the nucleic acid construct, further comprising a linker sequence being interposed between the first and the second polynucleotide segments.

According to still further features in the described preferred embodiments the linker sequence is selected from the group consisting of an IRES encoding sequence and a protease cleavage recognition site encoding sequence.

According to still further features in the described preferred embodiments the at least one promoter is functional in eukaryotic cells.

According to still further features in the described preferred embodiments the at least one promoter is selected from the group consisting of a constitutive promoter, an inducible promoter and a tissue specific promoter.

According to still further features in the described preferred embodiments the nucleic acid expression construct, further comprising: (c) a first promoter sequence being for directing the expression of the first polynucleotide segment; and (d) a second promoter sequence being for directing the expression of the second polynucleotide segment.

According to still further features in the described preferred embodiments the first promoter and the second promoter are each independently selected from the group consisting of a constitutive promoter, an inducible promoter and a tissue specific promoter.

According to still further features in the described preferred embodiments the first and the second growth factors are each independently selected from the group consisting of vascular endothelial growth factor (VEGF), hepatocyte growth factor (HGF), fibroblast growth factor 1 (FGF 1), fibroblast growth factor 2 (FGF 2) and Platelet derived growth factor (PDGF). According to yet another aspect of the present invention there is provided a genetically transformed cell comprising the nucleic acid expression construct(s) described above.

According to still further features in the described preferred embodiments the transformed cell is selected from the group consisting of an hepatocyte cell or a progenitor thereof and an endothelial cell or a progenitor thereof.

According to still further features in the described preferred embodiments the endothelial cell is derived from a source selected from the group consisting of a segment of a liver, a segment of a vein, bone marrow progenitor cells, peripheral blood stem cells, circulating endothelial cells and embryonic stem cells.

According to still further features in the described preferred embodiments the transformed cell is derived from a source selected from the group consisting of a human donor and an animal source.

According to still another aspect of the present invention there is provided a population of cells transformed with at least one nucleic acid expression construct being capable of expressing at least two distinct growth factors.

According to still further features in the described preferred embodiments the population of cells is transiently or stably transformed with the at least one nucleic acid construct.

According to still further features in the described preferred embodiments the population of cells includes at least two cell types selected from the group consisting of hepatocytes cells, endothelial cells, allogeneic liver cells and progenitor cells.

According to still further features in the described preferred embodiments each cell type of the at least two cell types is genetically transformed to express one specific growth factor of the at least two distinct growth factors.

According to still further features in the described preferred embodiments the first cell type is an hepatocyte cell and further wherein the second cell type is an endothelial cell and vice versa.

According to still further features in the described preferred embodiments the endothelial cell is derived from a source selected from the group consisting of venous tissue, arterial tissue, fat tissue, progenitor cells, circulating endothelial cells, and bone marrow stem cells, liver tissue and progenitor cells.

According to still further features in the described preferred embodiments expression of each growth factor of the at least two distinct growth factors is independently regulatable.

According to still further features in the described preferred embodiments the at least two distinct growth factors are each independently selected from the group consisting of VEGF, HGF, FGF 1, FGF 2, and PDGF.

According to an additional aspect of the present invention there is provided a method of inducing liver regeneration in a damaged liver tissue region of an individual, the method comprising the step of providing at least two distinct growth factors to the damaged liver tissue region of the individual, at least one of the at least two distinct growth factors being an angiogenic factor.

According to still further features in the described preferred embodiments the step of providing the at least two distinct growth factors to the damaged liver tissue region of the individual is effected by administering to the individual at least one nucleic acid construct being capable of expressing the at least two distinct growth factors.

According to still further features in the described preferred embodiment the step of providing the at least two distinct growth factors to the damaged liver tissue region of the individual is effected by administering to the damaged liver tissue region of the individual a population of cells being capable of expressing and optionally secreting the at least two distinct growth factors.

According to still further features in the described preferred embodiments the method is utilized for treating or alleviating liver damage in an individual.

According to still further features in the described preferred embodiments the method is utilized for treating or preventing portal hypertension.

According to still further features in the described preferred embodiments the individual is human being.

According to still further features in the described preferred embodiments the population of cells includes at least two cell types.

According to still further features in the described preferred embodiments the cell or cells used are derived from the individual to be treated.

According to still further features in the described preferred embodiments the at least two cell types are each independently selected from the group consisting of hepatocytes cells or their progenitors, and endothelial cells or their progenitors.

According to still further features in the described preferred embodiments the at least two distinct growth factors are each independently selected from the group consisting of VEGF, HGF, PDGF, FGF 1 and FGF 2.

According to still an additional aspect of the present invention there is provided a delivery catheter comprising: (a) an elongated body having open proximal and distal ends defining a flowthrough passage therebetween, the elongated body being sized and constructed for positioning within a biological vessel; and (b) an inflatable balloon being attached to, or forming a part of, a circumferential surface portion of the elongated body, the inflatable balloon being designed and constructed for sealing a space formed between the circumferential surface portion of the elongated body and adjacent walls of the biological vessel when inflated, thereby preventing flow back of material delivered through the flowthrough passage.

According to still further features in the described preferred embodiments the delivery catheter further comprising an injection port being in fluid communication with the inflatable balloon and being positioned outside the body when the elongated body is positioned within the biological vessel.

According to still further features in the described preferred embodiments the delivery catheter further comprising a delivery port being in fluid communication with the flowthrough passage and being positioned outside the body when the elongated body is positioned within the biological vessel.

The present invention successfully addresses the shortcomings of the presently known configurations by providing a nucleic acid constructs, hepatocytes and endothelial cells transformed therewith, a catheter for delivering such constructs and transformed cells and methods of utilizing such constructs and transformed cells for inducing hepatocytes proliferation and liver regeneration.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of s example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 illustrates a delivery catheter according to an embodiment of the present invention.

Figure 2A:
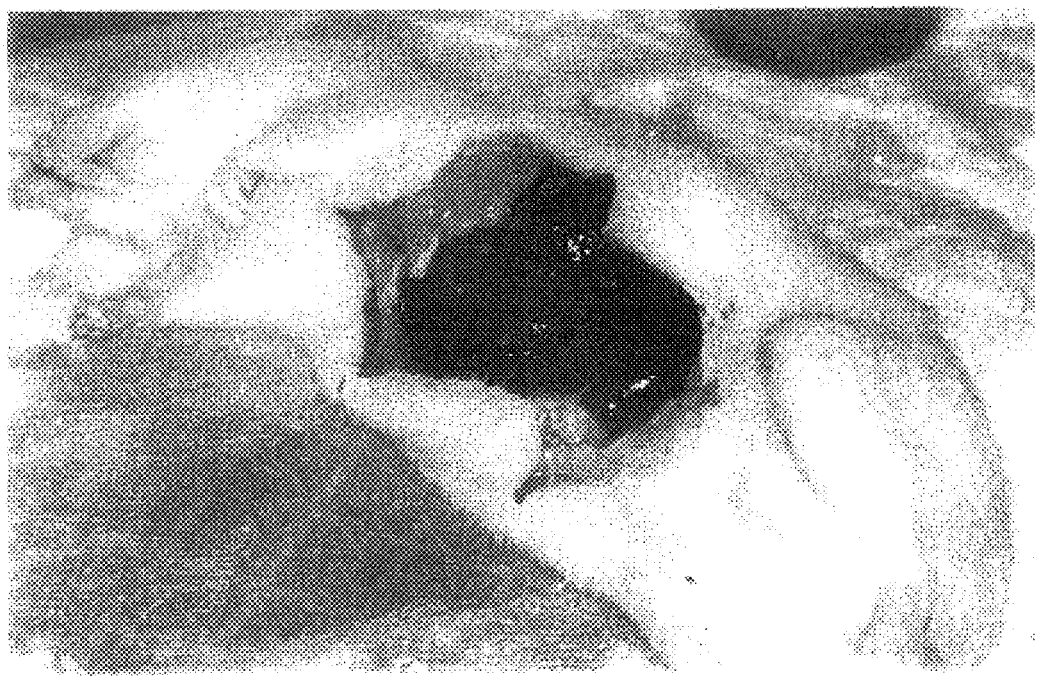
Figure 2B:
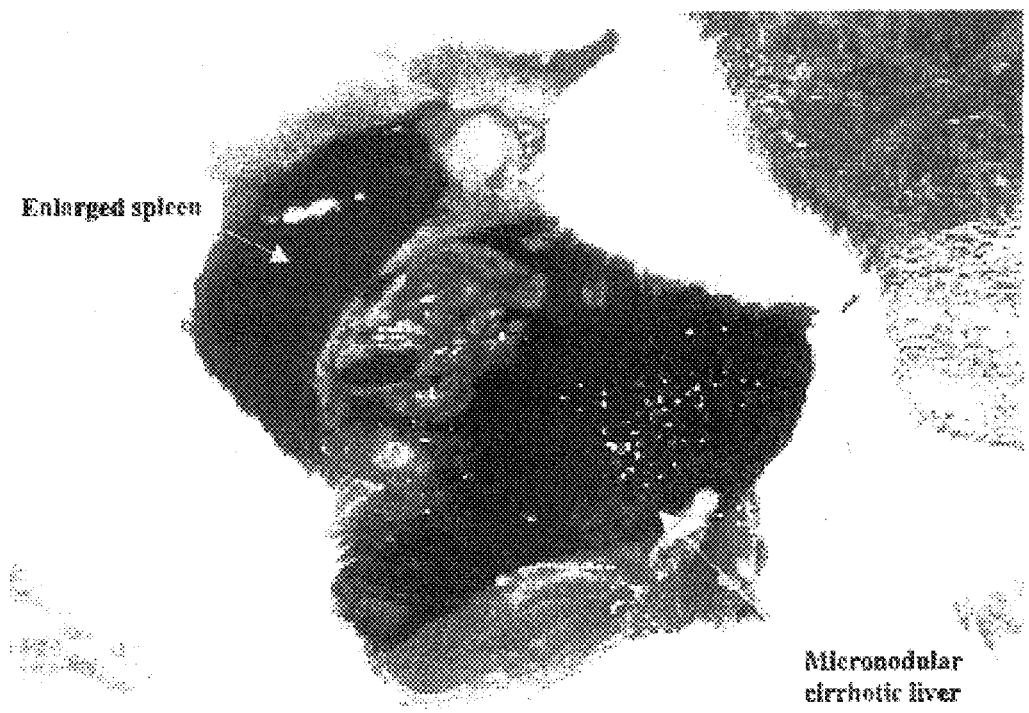

FIGS. 2a-b illustrate a cirrhotic liver and an enlarged spleen of a rat treated for 16 weeks with intra-peritoneal injections of CCl4/olive oil (1 ml/kg body weight) (FIG. 2a). FIG. 2b is a closer view of the same field shown in FIG. 2a.

Figure 3:
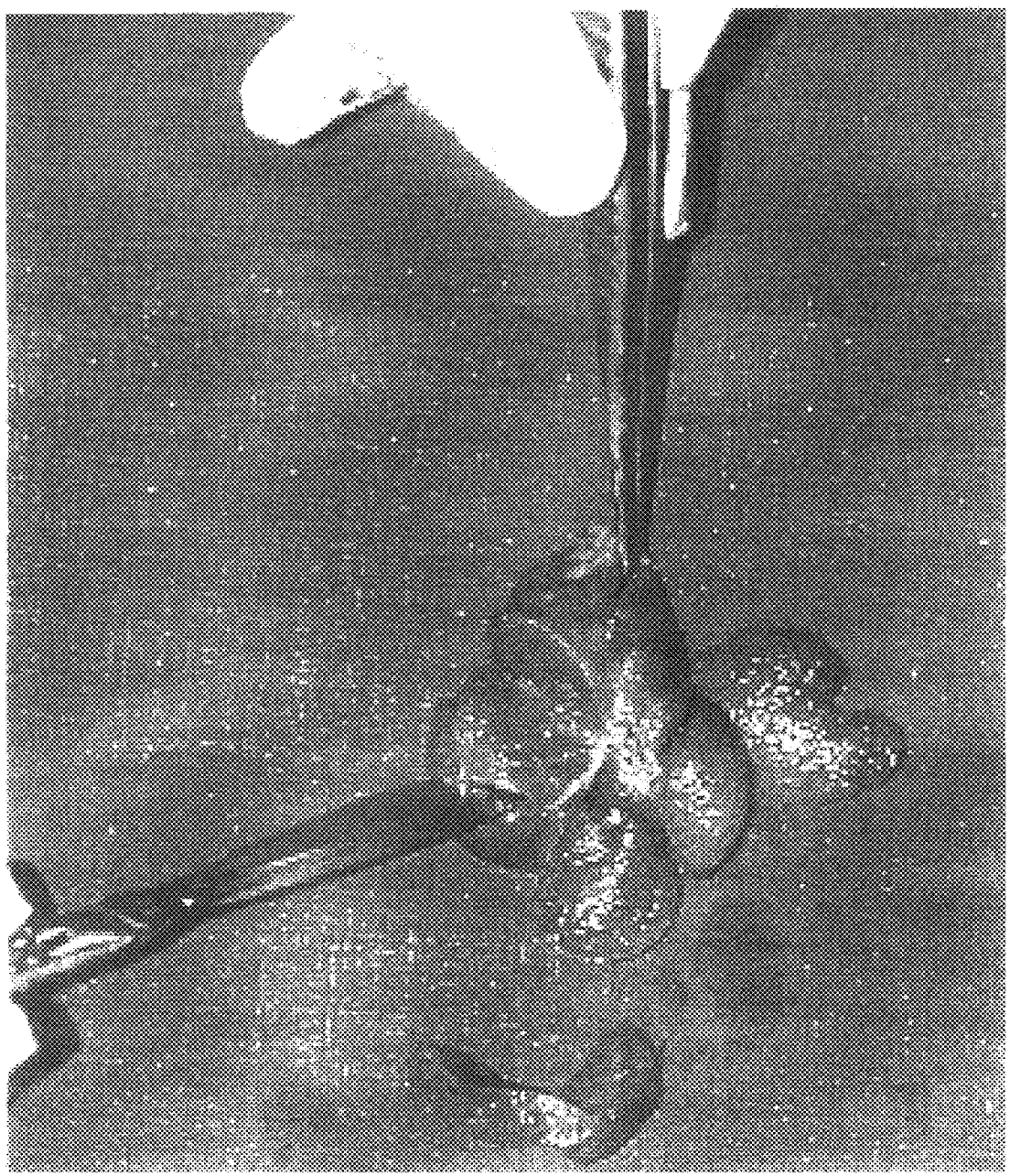

FIG. 3 illustrates the gross appearance of a rat cirrhotic liver which has been removed from the rat body.

Figure 4A:
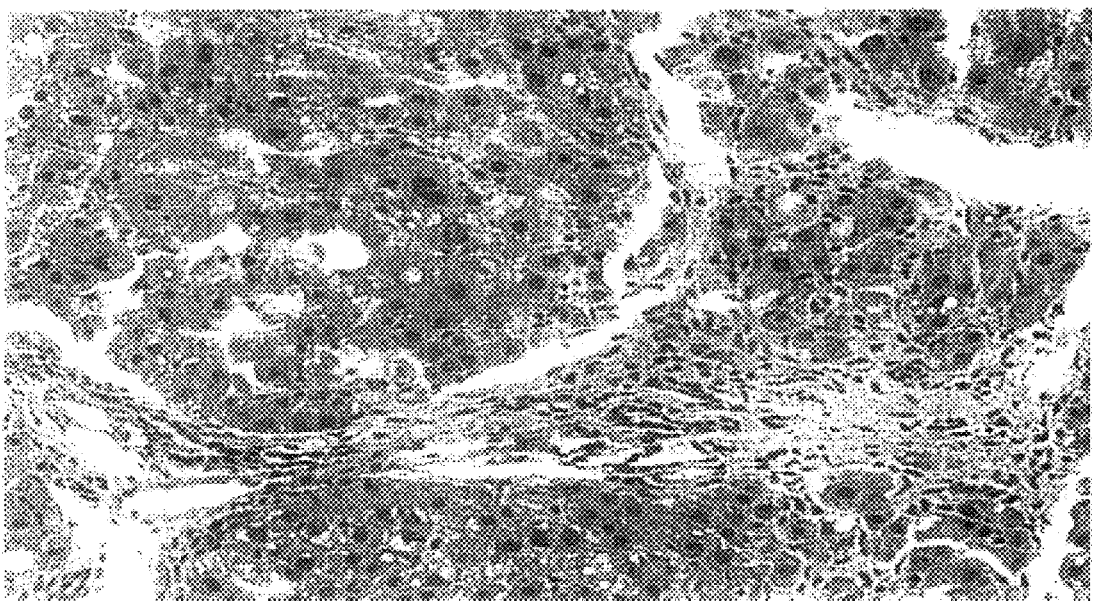
Figure 4B:
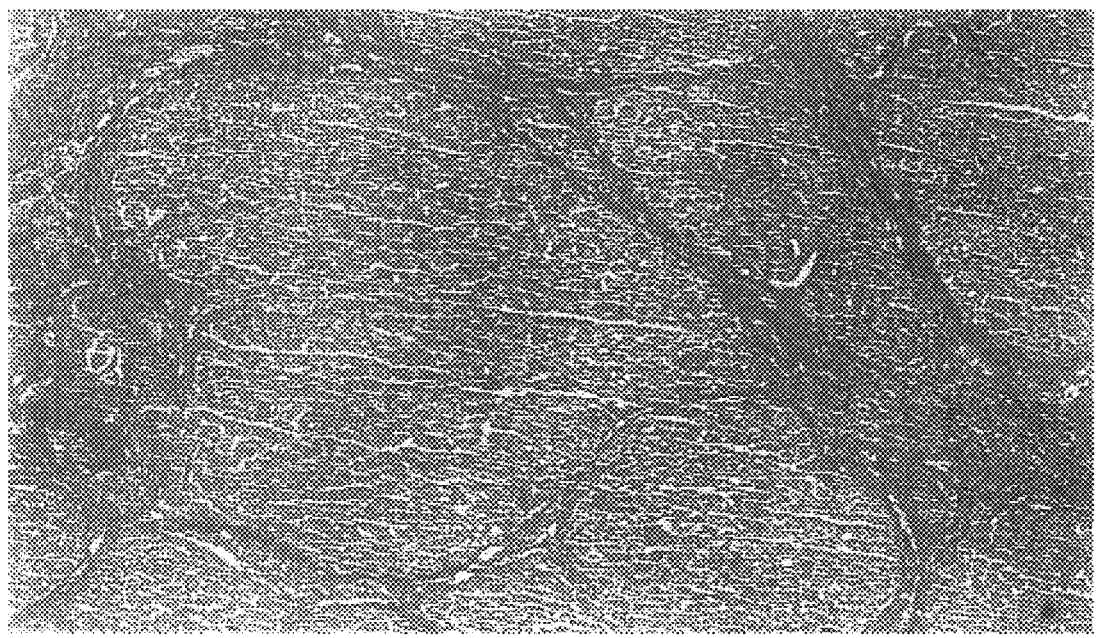
Figure 4C:
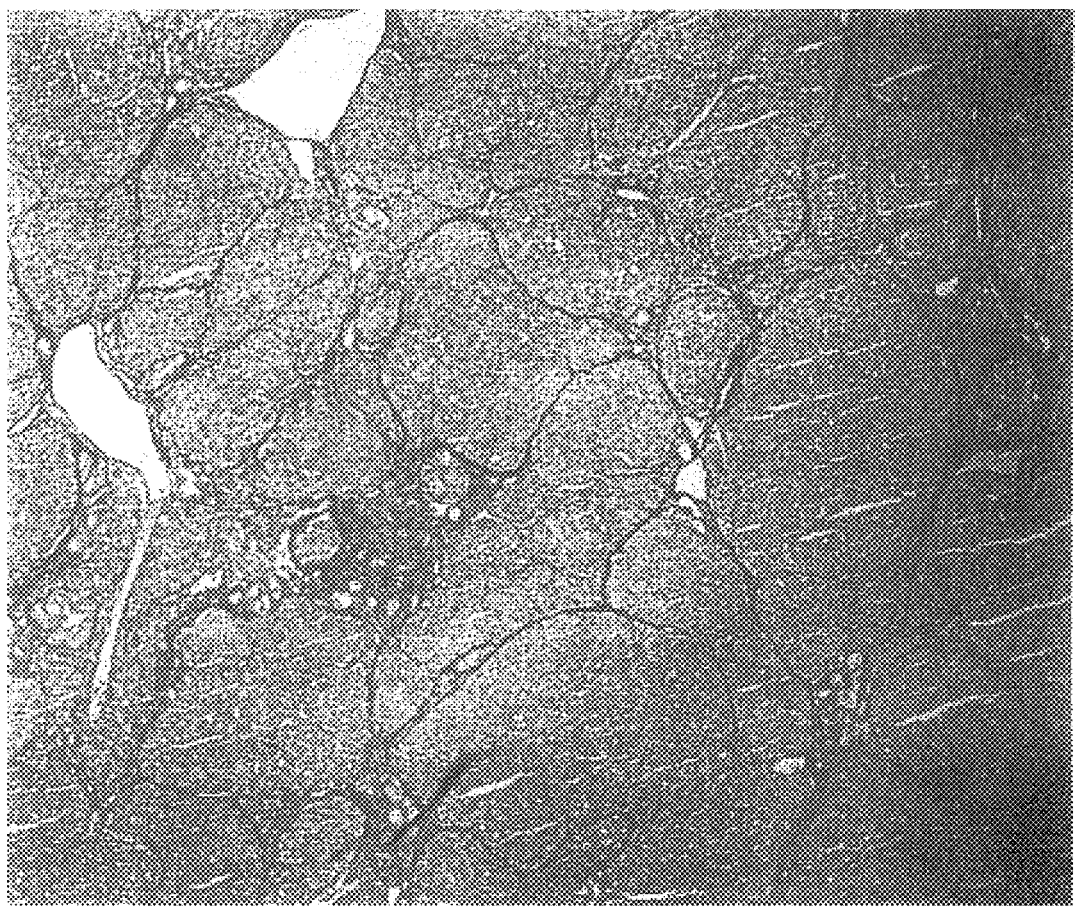

FIGS. 4a-c illustrate an Elastica/vonGiesson staining histology pattern of tissue derived from liver of three rats having complete liver cirrhosis.

FIGS. 5a-b illustrate β-galactosidase activity measured three days following infection of human hepatoma cultured cells (HuH-7) with Ad5.CMV-LacZ adenovirus. FIG. 5b is a magnification of a field shown in FIG. 5a.

FIGS. 6a-b illustrate β-galactosidase activity of liver tissue sections obtained from normal rat livers seven days following transduction thereof with the recombinant Ad5.CMV-LacZ adenovirus of the present invention. FIG. 6b is a magnification of a field shown in FIG. 6a.

Figure 7A:
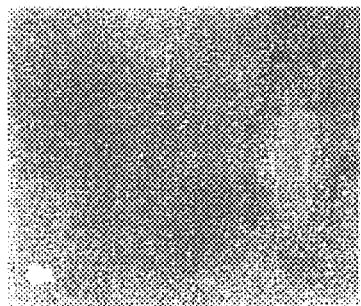
Figure 7B:
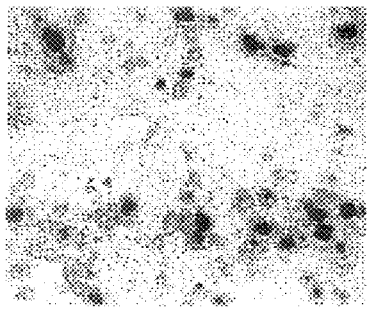
Figure 7C:
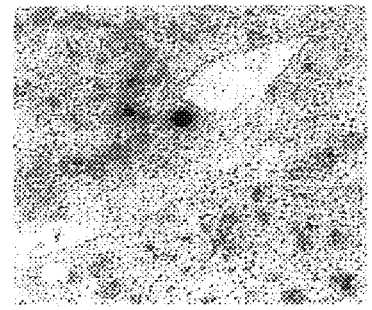

FIGS. 7a-c illustrate β-galactosidase activity in liver sections obtained from a fibrotic liver seven days following infection with recombinant Ad5.CMV-LacZ adenovirus. FIGS. 7b-c are magnified views of a field shown in FIG. 7a.

Figure 8A:
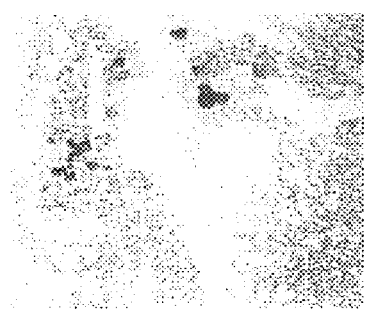
Figure 8B:
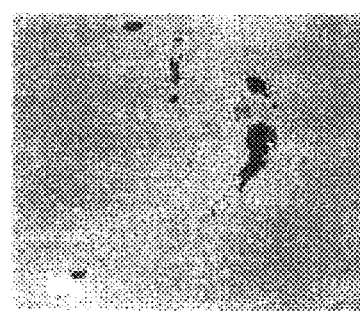
Figure 8C:
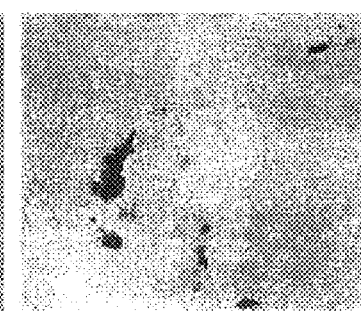

FIGS. 8a-c illustrate β-galactosidase activity in liver sections obtained from a cirrhotic liver seven days following infection with recombinant Ad5.CMV-LacZ adenovirus. FIGS. 8b-c are magnified views of a field shown in FIG. 8a.

Figure 9:

FIG. 9 illustrates a pressure measurement system used for determining the portal vein pressure of the cirrhotic, fibrotic or normal rats used by the present invention.

Figure 10A:
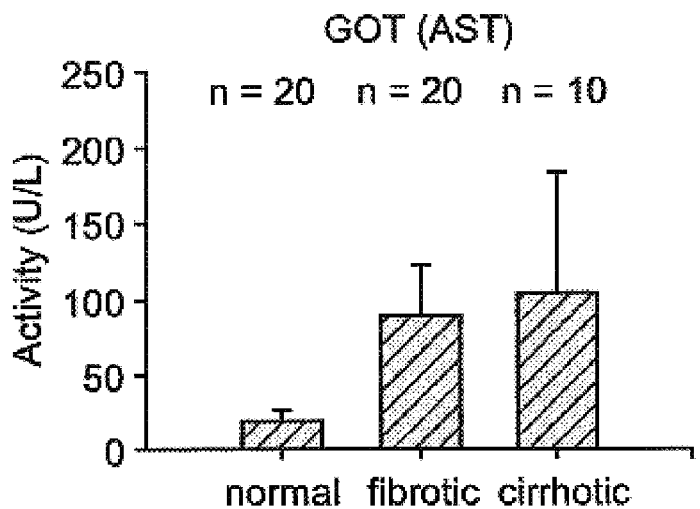
Figure 10B:
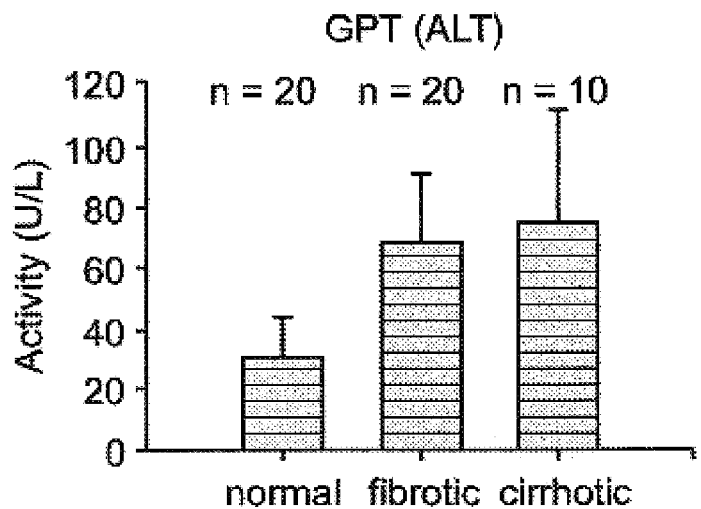
Figure 10C:
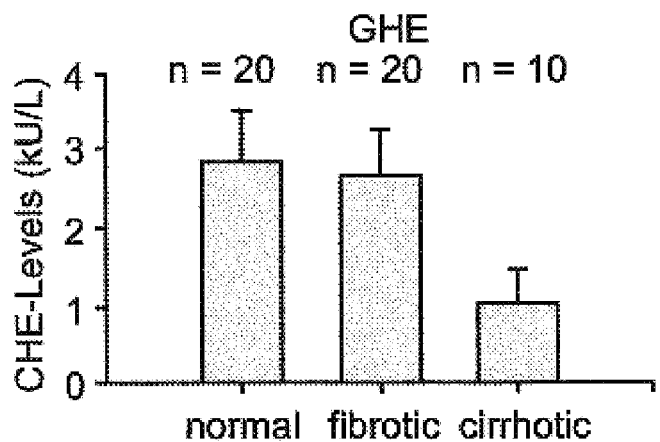

FIGS. 10a-c illustrate enzyme activity in blood serum drawn from a rat tail vein at the time of Ad5.CMV-LacZ injection or at the time of portal pressure measurement. Asparate aminotransferase-AST (FIG. 10a), alanine aminotransferase-ALT (FIG. 10b) and cholinesterase-CHE (FIG. 10c) activities are represented in mean values and standard deviations of results in normal (n=20), fibrotic (n=20) and cirrhotic animals (n=10).

Figure 11A:
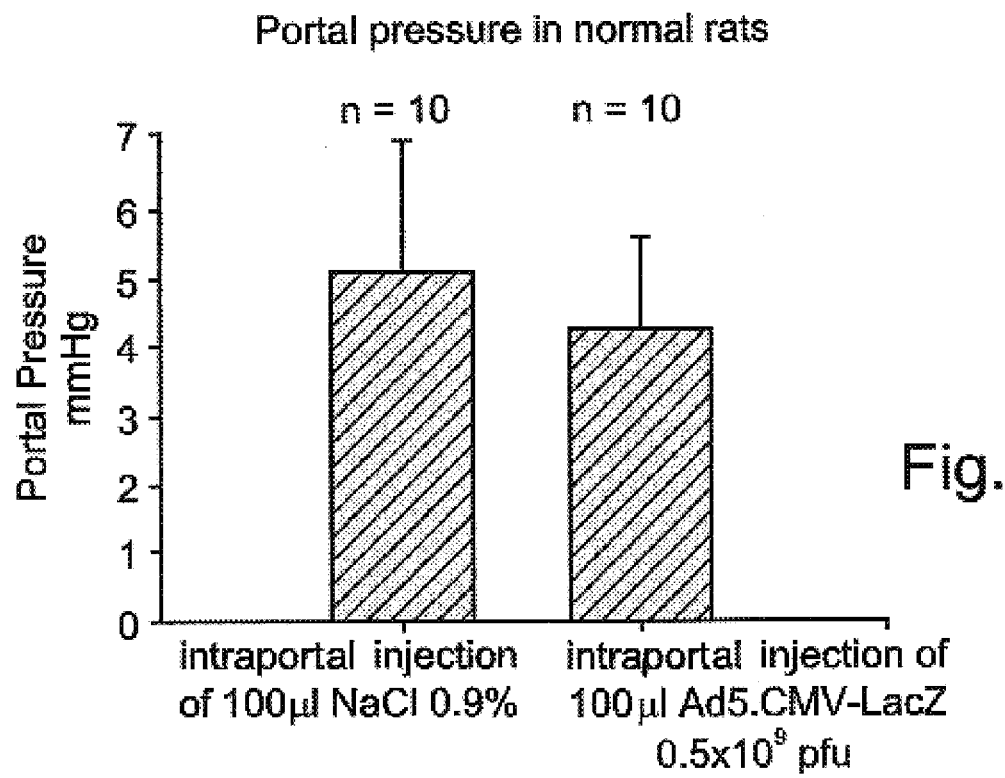
Figure 11B:
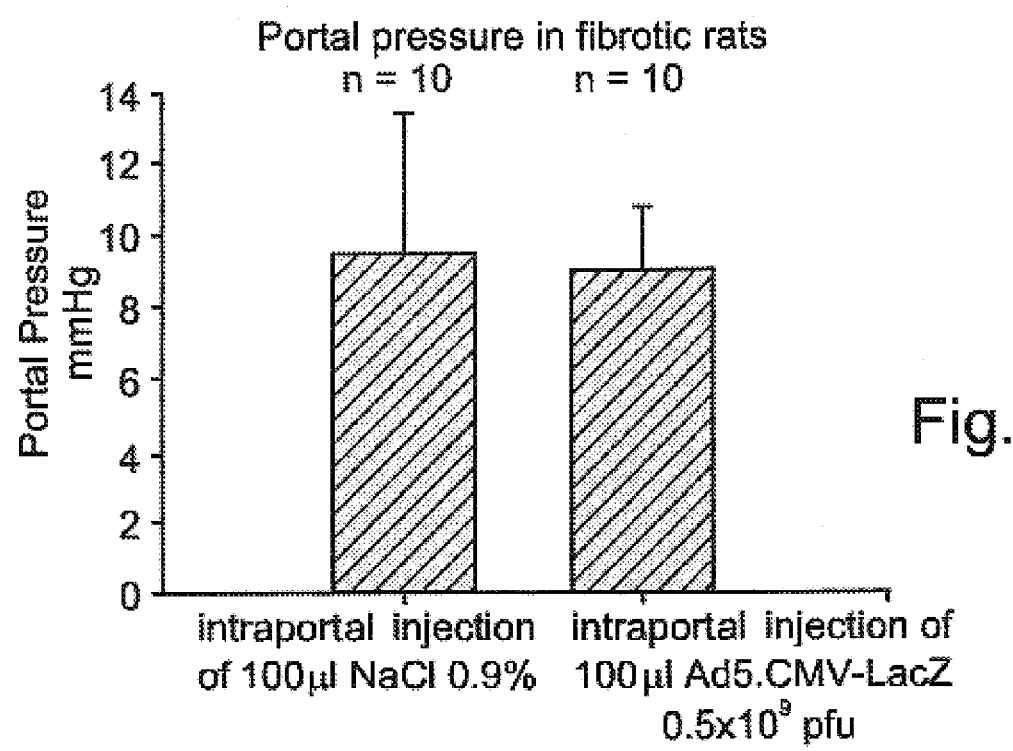
Figure 11C:
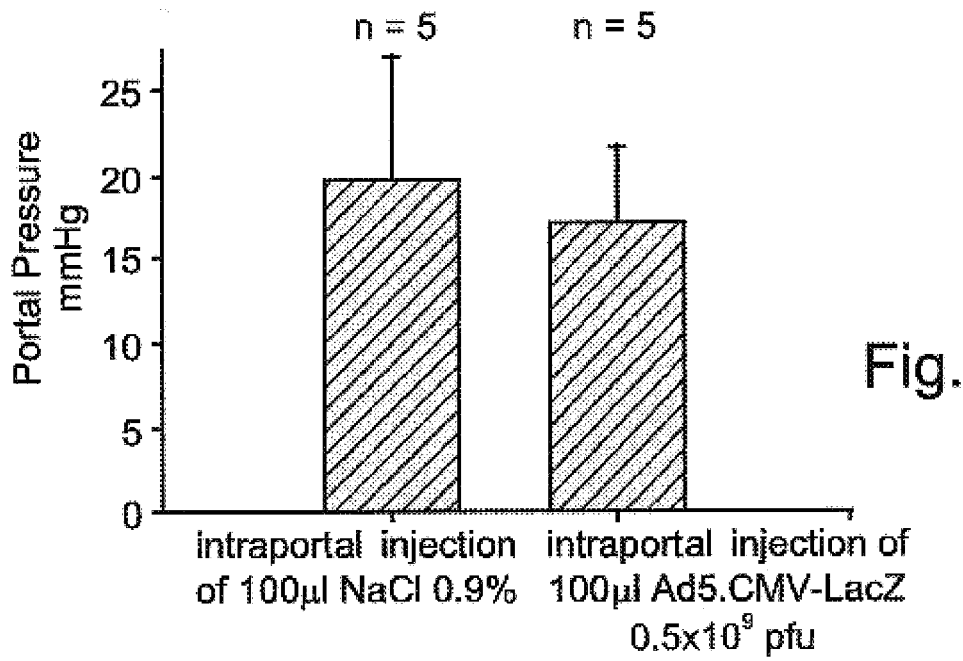

FIGS. 11a-c illustrate portal blood pressure readings of normal animals (FIG. 11a), fibrotic animals (FIG. 11b), and cirrhotic animals (FIG. 11c) seven days following intraportal injection of 100 μl NaCl 0.9% (placebo, n=10) or 100 μl 0.5×10$^9$ pfu Ad5.CMV-LacZ adenovirus (n=10). Values represented as mean values plus standard deviations.

Figure 12:
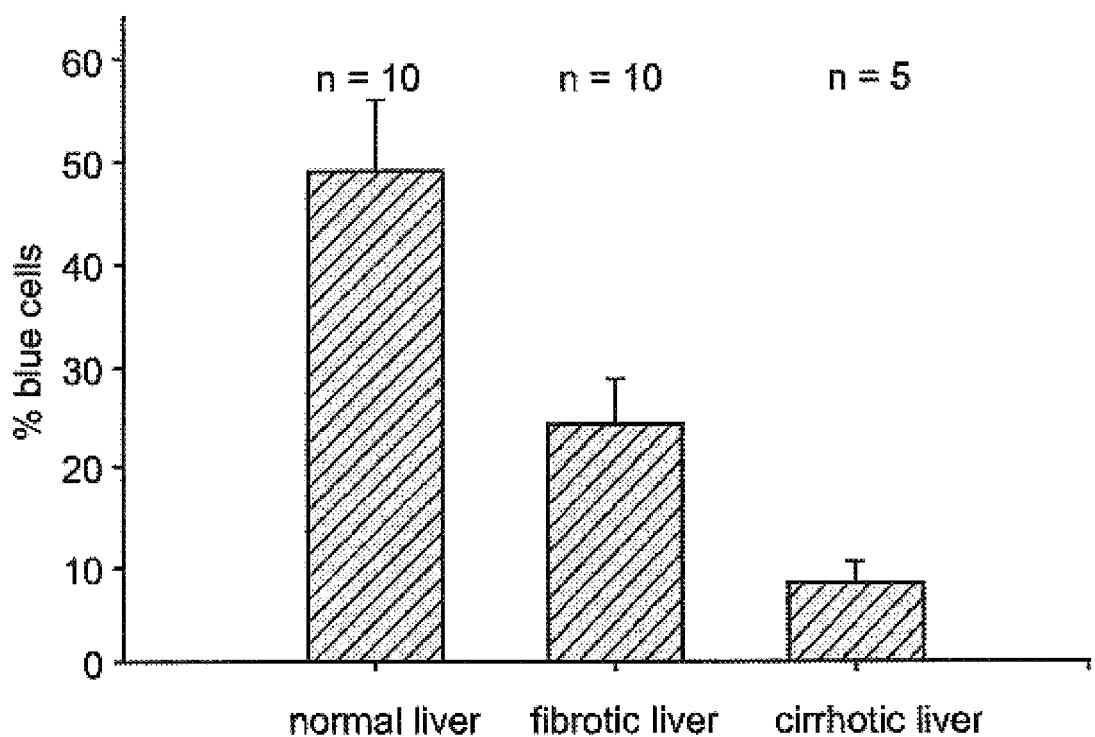

FIG. 12 is a graph representing the number of Ad5.CMV-LacZ transduced cells which express β-galactosidase in a liver section of normal animals (n=10), fibrotic animals (n=10) and cirrhotic animals (n=5). Values are represented as percent of total cells per microscopic field of view which express β-galactosidase. Five fields were counted for each rat; mean levels and standard deviations were calculated for each group of animals; normal animals, n=10; fibrotic animals, n=10 and cirrhotic animals, n=5.

Figures 13A, 13B:
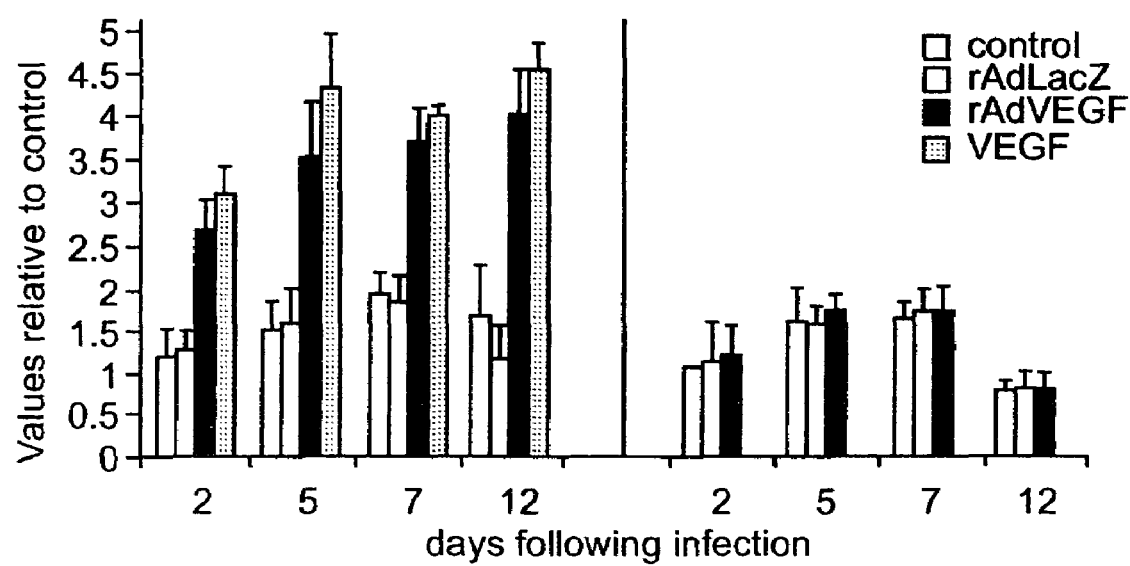

FIGS. 13a-b illustrate the effect of infection with recombinant adenoviral vector encoding VEGF (rAdVEGF) on the proliferation rate of Human Saphenous Vein Endothelial Cells (HSVEC) (FIG. 13a) and human saphenous vein smooth muscle cells (HSVSMC) (FIG. 13b). HSVEC (5×10$^4$ cells/35 mm) and HSVSMC (10$^5$ cells/35 mm) were seeded 24 hours prior to infection with the adenoviral vectors of the present invention. Cells infected with: (i) rAdVEGF (black bars), (ii) rAdlacZ (dashed bars), or uninfected control cells (white bars) were cultured for 12 days following infection while uninfected HSVEC cells were grown in the presence of recombinant human $VEGF_{165}$ (10 ng/ml) (gray bars). Cell proliferation was measured via cell counting at 2, 5, 7 and 12 days following adenoviral infection. Values are represented as mean±S.E of the four different experiments performed.

Figure 14A:
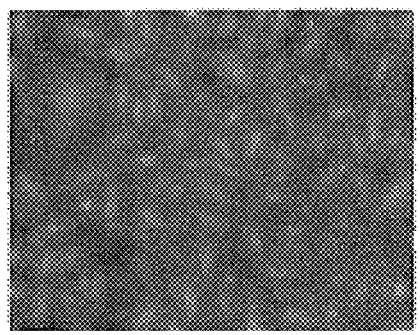
Figure 14B:
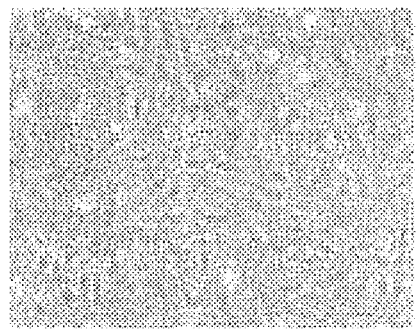
Figure 14C:
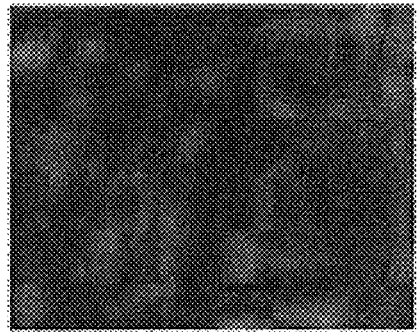
Figure 14D:
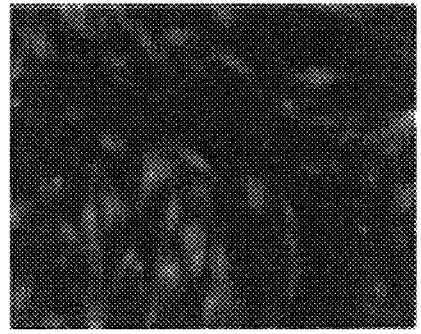

FIGS. 14a-d illustrate ECs and SMCs co-infected with HSVEC (FIG. 14b), mpJVSMC (FIG. 14c) or mpJVEC (FIG. 14d) and rAdHGF-GFP and ECs and SMCs infected with rAdHGF-GFP alone (FIG. 14a). The cells were visualized by a fluorescent inverted microscope (FIGS. 14a, c and d) or by a light inverted microscope (FIG. 14b).

Figure 15A:
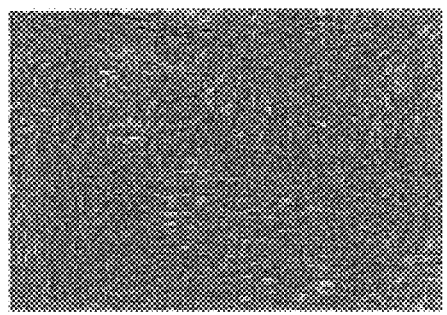
Figure 15B:
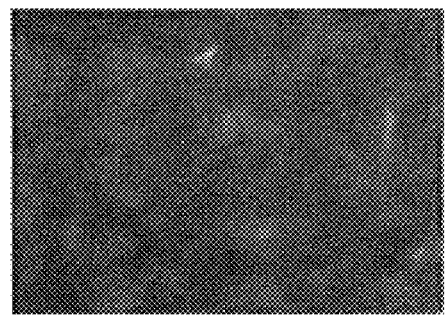
Figure 15C:
Figure 15D:

FIGS. 15a-d illustrate ECs and SMCs transduced with retro HGF-GFP. mp JVECEC (FIGS. 15a-b) or with mp FASMC and retro HGF-GFP (FIGS. 15c-d). The cells were visualized by either light inverted microscope (FIGS. 15a and c)) or by fluorescent inverted microscope (FIGS. 15b and d).

Figure 16:
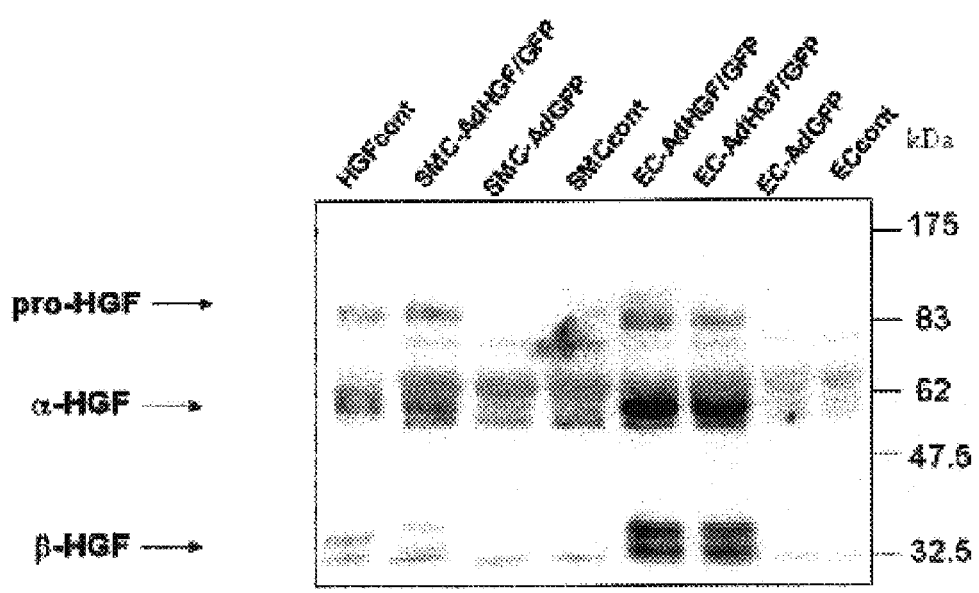

FIG. 16 illustrates a Western blot analysis of HGF expression in rAd infected ECs and SMCs. Infected cells were grown for 24 hrs in serum free medium. Samples of the growth medium (30 µl) were loaded on 8% SDS polyacrylamide gel, transferred to nitrocellulose membrane and the blots were incubated with anti-HGF antibody. Following exposure to a peroxidase-conjugate secondary antibody the blots were developed with ECL reagents and exposed to X-ray film.

Figure 17:
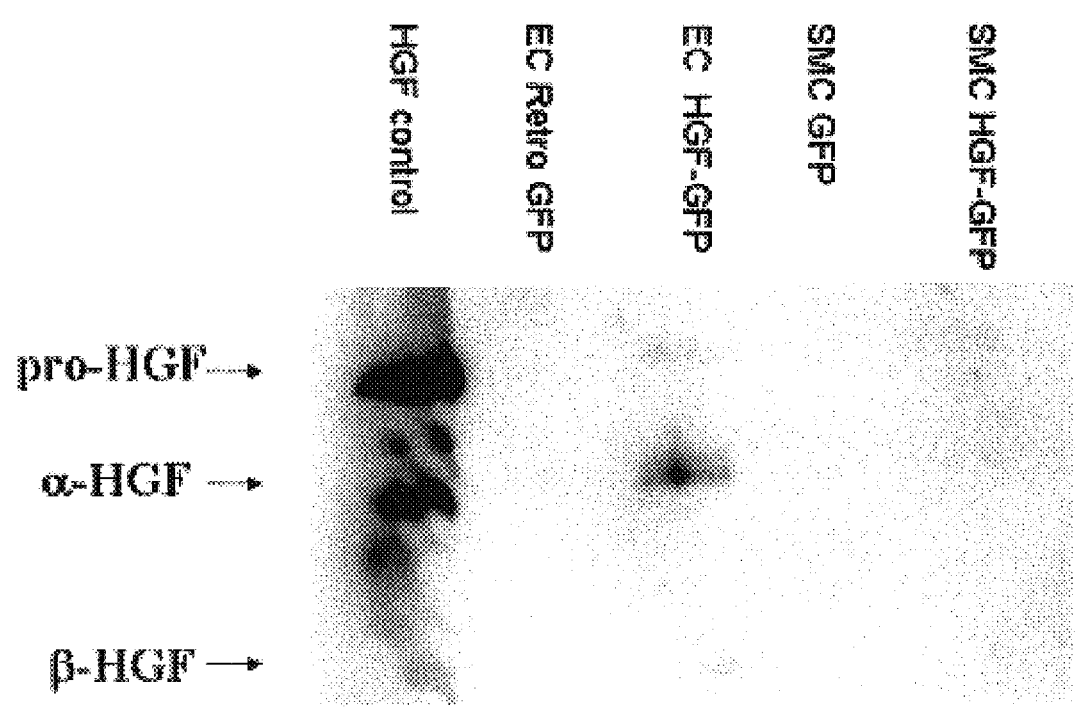

FIG. 17 illustrates a Western blot analysis of HGF expression in retro transduced ECs and SMCs. Transduced cells were grown for 24 hrs in serum free medium. Samples of the growth medium (30 µl) were loaded on 8% SDS polyacrylamide gel, transferred to nitrocellulose membrane and the blots were incubated with anti-HGF antibody. Following exposure to a peroxidase-conjugate secondary antibody the blots were developed with ECL reagents and exposed to X-ray film.

Figure 18A:
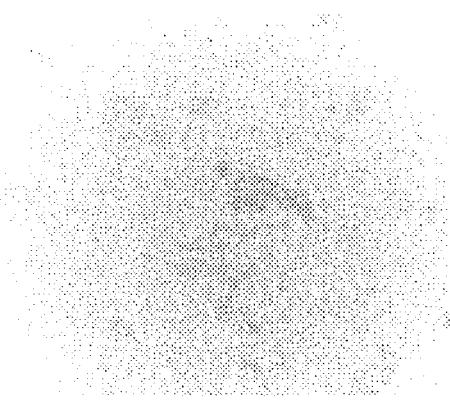
Figure 18B:
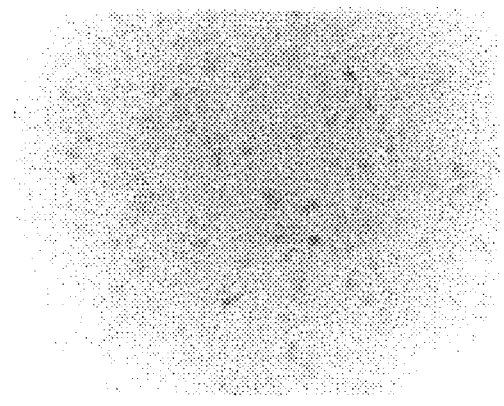
Figure 18C:
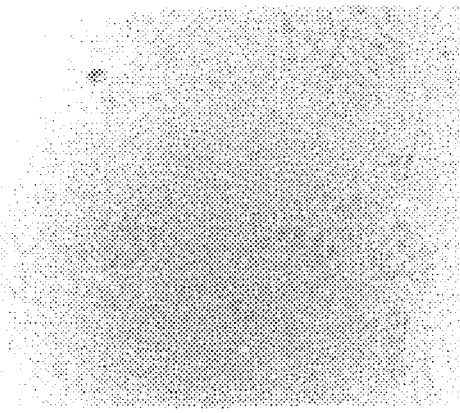
Figure 18D:
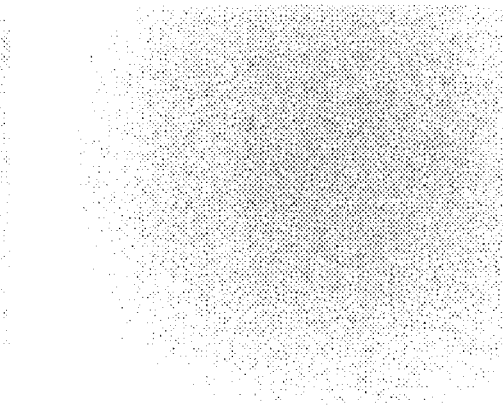

FIGS. 18a-d illustrate a scatter assay conducted to determine biological activity of HGF expressed from the Adeno vector described herein. A 1 µl sample was collected from the condition medium of 293 cells (FIG. 18a), 293 Adeno HGF/GFP producing cells (FIG. 18b) or 293 Adeno GFP producing cells (FIG. 18c). The sample was diluted in 100 µl of DMEM, 5% FCS and added to seeded MDCK cells. rhHGF diluted in 100 µl of DMEM, 5% FCS to a concentration of 10 ng/ml was used as a positive control (FIG. 18d). Following overnight incubation, 4% PFA fixation, and H&E staining, the MDCK cells were visualized by light inverted microscope.

Figure 19A:
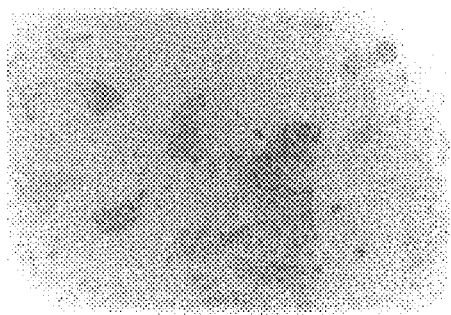
Figure 19B:
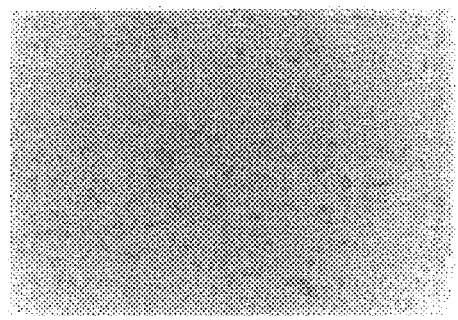

FIGS. 19a-b illustrate a scatter assay conducted to determine the biological activity of retrovirally expressed HGF. A 100 µl sample was collected from the condition medium of 293flyGALV cells (FIG. 19a) or 293flyGALV-HGF/GFP cells (FIG. 19b) and added to MDCK cells as described above. Following overnight incubation, 4% PFA fixation, and H&E staining, the cells were visualized using a light inverted microscope.

Figures 20, 20A:
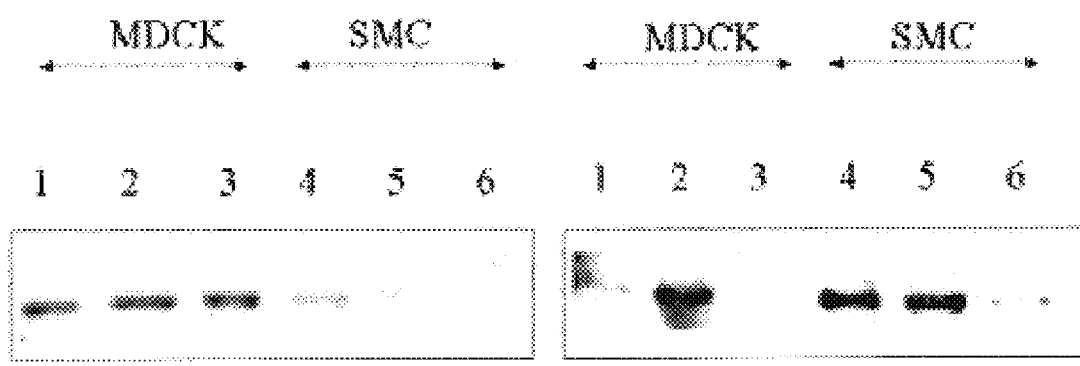

FIGS. 20a-b illustrate phosphorylation of cMET receptor. FIG. 20a—MDCK cells (lanes 1-3) and SMC cells (lanes 4-6) were seeded in 60 mm plates at ~90% confluence and grown in serum free media supplemented with 5 mg/ml Transferrin and 5 mg/ml Insulin for 24 hrs. The cells were incubated for 15 min at 37° C. with 30 ml of a condition medium collected from 293 cells expressing rAdHGF-GFP (lanes 2 and 5) or rAdGFP (lanes 3 and 6). 30 ng/ml of recombinant human HGF were used as a positive control (lanes 1 and 4). The cells were lysed and samples containing equal amounts of protein were analyzed using anti-cMET antibodies as described in the Examples section hereinunder. FIG. 20b—lysate from each of the EC adeno infected cell type was subjected to immunoprecipitation using an anti-phosphotyrosine antibody as is further described in the Examples section which follows. Immunoprecipitates were solubilized in SDS/PAGE sample buffer, chromatographed on 6% SDS-PAGE gel followed by Western blot analysis using anti-cMET antibodies. Lanes: 1 and 4—recombinant human HGF, lanes 2 and 5—condition medium of 293 rAdHGF-GFP, lanes 3 and 6—condition medium of 293 rAdGFP.

DESCRIPTION OF THE PREFERRED EMBODIMENTS

The present invention is of nucleic acid constructs, cells transformed therewith which can be used for inducing liver regeneration in a damaged liver. More specifically, the present invention can be used for enhancing liver regeneration and angiogenesis of sinusoidal capillaries in mammalian liver tissue, thus promoting liver regeneration while decreasing portal hypertension and cell death.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Current treatment methods for cirrhosis-related liver damage offer solutions for only some of the complications resulting from liver damage while being ineffective in reversing liver damage and restoring normal liver function.

The present inventors propose a novel method for treating cirrhosis in individuals at risk, and for inducing and enhancing liver regeneration in individuals suffering from liver damage and cirrhosis.

The present invention utilizes two distinct growth factors including at least one angiogenic factor, for enhancing liver cell proliferation, capillary production, and formation of sinusoidal network thus inducing liver tissue regeneration and alleviating portal hypertension.

As used herein the phrase "growth factor" refers to a protein factor capable of recruiting or mobilizing cells to a site of tissue growth and/or capable of inducing cell proliferation and/or maturation.

As used herein the term "angiogenic factor" refers to a growth factor which directs or participates in the process of blood vessel formation and/or maturation.

Thus, according to one aspect of the present invention there is provided a nucleic acid expression construct including a first polynucleotide segment encoding a first growth factor and a second polynucleotide segment encoding a second growth factor, wherein at least one of the first and the second growth factors is an angiogenic factor.

Preferably, the first growth factor is an angiogenic factor such as but not limited to VEGF, while the second growth factor is an hepatocyte proliferating factor such as, but not limited to, HGF or HHGF. The co-expression of these factors in a predetermined spatial or temporal fashion can be used to induce proliferation of hepatocytes and sinusoidal as well as other endothelial cells thus synergistically contributing to liver tissue regeneration.

It will be appreciated that various construct schemes can be utilized to express both growth factors from a single nucleic acid construct.

For example, the two growth factors can be co-transcribed as a polycistronic message from a single promoter sequence of the nucleic acid construct. To enable co-translation of both growth factors from a single polycistronic message, the first and second polynucleotide segments can be transcriptionally fused via a linker sequence including an internal ribosome entry site (IRES) sequence which enables the translation of the polynucleotide segment downstream of the IRES sequence. In this case, a transcribed polycistronic RNA molecule including the coding sequences of both the first and the second growth factors will be translated from both the capped 5' end and the internal IRES sequence of the polycistronic RNA molecule to thereby produce both the first and the second growth factors.

Alternatively, the first and second polynucleotide segments can be translationally fused via a protease recognition site cleavable by a protease expressed by the cell to be transformed with the nucleic acid construct. In this case, a chimeric polypeptide translated will be cleaved by the cell expressed protease to thereby generate both the first and the second growth factors.

Still alternatively, the nucleic acid construct of the present invention can include two promoter sequences each being for separately expressing a specific growth factor of the two growth factors described above. These two promoters which can be identical or distinct can be constitutive, tissue specific or regulatable (e.g. inducible) promoters functional in one or more cell types.

The use of two distinct promoters enables differential temporal and/or spatial expression of the two distinct growth factors.

It will be appreciated that the expression of the two distinct growth factors can be directed from an expression construct system, which includes a dedicated expression construct for each growth factor.

To generate the nucleic acid construct(s) of the present invention, the polynucleotide segments encoding the two distinct growth factors (see Table 1 of the Examples section for further detail) can be ligated into a commercially available expression vector system suitable for transforming mammalian cells and for directing the expression of these factors within the transformed cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

Suitable mammalian expression vectors for use with the present invention include, but are not limited to, pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

According to preferred embodiments of the present invention, the nucleic acid constructs described hereinabove are used in in-vivo or ex-vivo transformation of liver cells or tissue.

As used herein the term "transformation" or the phrase "genetic transformation" refer to a cell transiently or stably transformed with exogenous polynucleotide sequence(s). In stable transformation, the exogenous polynucleotide sequences integrate into the genome of the cell and as such are genetically inherited by daughter cells, whereas in transient transformation, the exogenous polynucleotide sequences exist in a transient manner as nuclear or cytoplasmic molecules and as such, are not genetically inherited by daughter cells.

In the in-vivo transformation approach (direct gene transfer) the nucleic acid constructs of the present invention are used to directly transform liver tissues or cells of an individual. In such an approach, the nucleic acid constructs of the present invention are preferably constructed from recombinant adenoviral vectors, which are well suited for direct gene transfer and expression in liver tissues and cells. For further description of such vectors see Example 1 of the examples section which follows. Adenoviral mediated gene transfer expression can generate sustained expression of the above described factors for a period of several weeks, sufficient for achieving a therapeutic effect.

Direct gene transfer techniques have several distinct advantages. They enables prolonged local expression, thus a "single shot therapy" which is easy to carry out can be anticipated (Folkman et al, 1998). The use of a recombinant adenoviral vector for direct gene transfer is particularly advantageous. In contrast to other methods of gene transfer, adenoviral vector mediated transfer is highly efficient and it generates a high level of expression of the transferred gene (Anderson et al, 1998; Lewis et al 1997 and Folkman et al, 1998). In addition, inflammation caused by adenoviral vectors can be overcome by improved vector design and various tolerance schemes (Ilan et al, 1998).

In the ex-vivo transformation approach, the nucleic acid constructs of the present invention are utilized to transform isolated mammalian cells such as, but not limited to, endothelial cells, hepatocytes cells or any progenitor cells of the above mentioned cells, which are implanted, following this transformation, into the damaged liver tissue.

The nucleic acid constructs of the present invention can be introduced into a uniform or mixed population of cells via any standard mammalian transformation method. Such methods include, but are not limited to, direct DNA uptake techniques, and virus or liposome mediated transformation (for further detail see, for example, "Methods in Enzymology" Vol. 1-317, Academic Press).

Preferably, more than one cell type is utilized by the present invention for treatment of damaged liver tissue.

Liver regeneration involves proliferation of both hepatocytes and sinusoidal endothelial cells which express several growth factors, as such the present invention utilizes a mixed population of cells which includes a first cell type, such as, a hepatocyte cell or any progenitor thereof and a second cell type, such as, an endothelial cell or any progenitor thereof, although a single cell type population including, for example, hepatocytes or endothelial cells can also be utilized.

The use of a mixed population of cells including both hepatocytes and endothelial cells is particularly advantageous since the presence of endothelial cells will enhance blood supply to liver tissues thus enhancing hepatocyte survival and regeneration of normal liver unit architecture and function.

Each cell type can be transformed to express a distinct growth factor or alternatively one or both of these cell types can express both growth factors.

The cells are preferably derived from of a liver segment, a segment of a vein, bone marrow progenitor cells, peripheral blood stem cells, circulating endothelial cells or embryonic stem cells of the individual to be treated or from tissue of a syngeneic or an allogeneic individual. It will be appreciated that xenogeneic cells can also be utilized for preparing the population of cells of the present invention providing measures are taken prior to, or during administration, so as to avoid rejection of such cells by the treated individual. Numerous methods for preventing or alleviating cell rejection are known in the art and as such no further detail is given herein.

Due to their function and location, implanted endothelial cells are more likely to trigger an immune response than implanted hepatocytes. As such, in order to significantly reduce the severity of an immune response resultant from cellular implantation, endothelial cells are preferably derived from the individual to be treated.

According to a preferred embodiment of the present invention, liver regeneration is effected using hepatocytes and endothelial cells transformed to express VEGF and HGF. Such an approach is advantageous since it substantially increases the odds for liver regeneration.

Endothelial cells produce urokinase plasminogen activator (U-PA) which cleaves HGF (hepatocyte growth factor) to its active form (see Example 6 of the Examples section which follows). HGF expression by endothelial cells will increase concentration of active HGF and thus liver regeneration. Co-expressing VEGF and HGF in a mixed cell population (e.g., endothelial cells expressing HGF thereby controlling hepatocytes, and hepatocytes expressing VEGF thereby controlling endothelial cell proliferation) will substantially enhance coordinated regeneration of a functional liver.

In addition, co-expression of VEGF and HGF, will improve cell survival, by protecting the transplanted cells from apoptosis which can be triggered in cells transplanted into cirrhotic liver tissue.

Finally, transplanting both endothelial cells and hepatocytes in failing livers ensures orchestrated cellular functions and thus improves the chances of liver tissue regeneration and re-establishment of liver function, both of which are dependent on formation of a specific tissue architecture.

Liver tissue implantation of the constructs or transformed cells of the present invention can be effected by, for example, direct injection thereof into a tissue region around or within the cirrhotic region to be treated. Such an injection can be effected by a delivery catheter such as the perfusion catheter manufactured by Boston Scientific (USA).

Thus, the present invention provides nucleic acid construct and cells expressing same which can be to induce liver tissue regeneration and thus to repair tissue damage caused by disease, trauma, or substance abuse.

Such constructs or transformed cells can be utilized to induce liver regeneration in a damaged liver tissue region of an individual, by administration thereof to the damaged liver tissue region of the individual.

As described hereinabove, the growth factors can be provided to the damaged liver tissue by either locally expressing them from a nucleic acid construct or constructs, or by administering ex-vivo transformed hepatocytes and sinusoidal or other endothelial cells which express and secrete the desired factors at the site of treatment.

In any case, the expression of the growth factors can be either constitutive or independently regulated depending on angiogenic factor needs of the damaged liver tissue region. Independent regulation can be achieved by utilizing inducible, growth specific or tissue specific promoter sequences. Examples of promoters which can be utilized by the present invention include chemically regulated promoters such as, for example, the tetracycline regulatable promoter system described in Agha-Mohammadi S, Lotze M T. J Clinical Investigations 2000; 105:1177-1183, and biomechanical regulated promoters such as the shear stress responsive element described by Resnick et al., in PNAS USA 90:4591-4595, 1993.

It will be appreciated that a regulatable promoter is selected such that regulation thereof can be effected following administration of the nucleic acid constructs or the transformed cells into the tissue region to be treated. Thus, promoters which are regulatable by conditions generated during liver regeneration, such as for example, forces associated with cell-to-cell interactions, or promoters which can be regulated by externally administered factors which can safely be provided to either the tissue region or the blood stream of the individual to be treated are preferred.

As mentioned hereinabove, the transformed cells or the nucleic acid constructs of the present invention can be delivered into the body via a catheter or any other suitable delivery device. Preferably, the constructs or transformed cells of the present invention are delivered directly into the portal vascular system using a specially adapted catheter.

Figure 1:
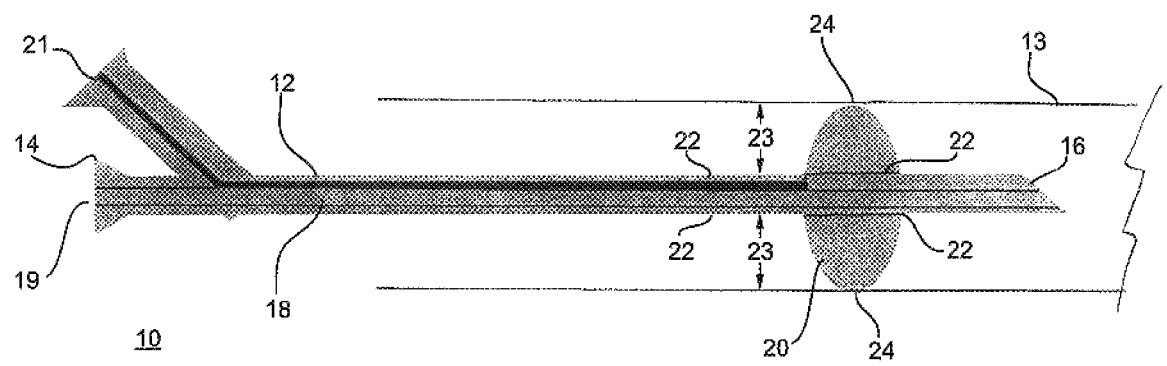

Thus, according to another aspect of the present invention and as specifically shown in FIG. 1, there is provided a delivery catheter which is referred to herein as catheter 10.

Catheter 10 includes an elongated body 12 having open proximal 14 and distal 16 ends which define a flowthrough passage 18 therebetween. Elongated body 12 is sized and constructed for positioning within a biological vessel (indicated by 13), which can be, for example, a blood vessel. To this end, elongated body 12 is preferably tubular in shape with a diameter selected within the range of 2 to 8 mm, depending on the application and biological vessel in which it is to be positioned. Elongated body 12 is constructed from a material or materials suitable for intrabody use such as, but not limited to, polyethylene (PE), polypropylene (PP), polyamides (nylon) and/or polyesters (PET).

Flowthrough passage 18 serves for delivering material such as a biological material including, for example, the constructs or cells of the present invention from outside the body into an area within the biological vessel which is situated upstream from the end of elongated body 12 through which delivery is effected.

Such delivery is preferably effected via a delivery port 19, which is in fluid communication with flowthrough passage 18 and which is preferably positioned outside the body when elongated body 12 is positioned inside the biological vessel.

Catheter 10 further includes an inflatable balloon 20 which is attached to, or forms a part of, a circumferential surface portion 22 of elongated body 12 (shown in an inflated position in FIG. 1).

Balloon 20 is inflatable via an injection port 21 which is in fluid communication with balloon 20; injection port 21 is preferably positioned outside the body when elongated body 12 is positioned inside the biological vessel. Inflation of balloon 20 can be effected via any fluid including air, gas (e.g., nitrogen) and liquid (e.g., saline).

Inflatable balloon 20 serves for preventing backflow of delivered material when in an inflated position. Such backflow can result from regurgitation of delivered material through a space or gap (indicated by 23) which forms between surface 22 and adjacent walls 24 of the biological vessel when catheter 10 is positioned within the vessel.

Inflation of balloon 20 serves for sealing such gap or space thus preventing flow back of delivered material.

This feature of catheter 10 is particularly advantageous especially in cases where localized delivery of material is preferred.

To enable delivery of the constructs or cells of the present invention into the liver, catheter 10 is inserted through a vein such as femoral vein and positioned using fluoroscopy in the portal vein. Once located within the portal vein, balloon 20 is inflated until a seal is established as indicated by lack of regurgitation of contrast media injected via flowthrough passage 18. After establishing occlusion of the portal vein, the constructs or cells of the present invention can be delivered. Following delivery, balloon 20 is deflated and catheter 10 is withdrawn.

Such delivery prevents unwanted backward distribution of the injected material to the spleen and other organs. This enables localized and efficient delivery of the constructs or transformed cells into hepatic tissue while at the same time preventing distribution thereof within other organs or tissues.

The constructs or cells of the present invention can also be delivered using prior art techniques, including, for example, the transjugular intrahepatic portosystemic shunt (TIPS) technique described by Rössle et al. (NEJM 2000; 342:1701-1707).

Thus, the present invention provides nucleic acid constructs, cells transformed therewith, a catheter for delivering each and methods of using the transformed cells or constructs for inducing liver tissue proliferation. As such, the present invention can be used to induce and/or enhance liver tissue regeneration, capillary angiogenesis, and sinusoidal network formation to thereby prevent or alleviate portal hypertension in cirrhosis and thus provide an alternative treatment strategy for a variety of serious liver diseases.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

The present invention utilizes nucleic acid constructs expressing VEGF and HGF for inducing hepatocytes proliferation and angiogenesis in damaged liver tissue. The Examples which follow outline methods for utilizing such constructs in enhancing liver regeneration and in promoting angiogenesis of sinusoidal capillaries in mammalian liver tissue.

Example 1

Preparation and Expression Analysis of Adenoviral Vectors Expressing the $VEGF_{165}$ cDNA, HGF cDNA and the Bacterial β Galactosidase Gene Recombinant adenoviral vectors expressing either bacterial Lac Z (β-galactosidase) (Weisz et al, Circulation 2001, in press), human $VEGF_{165}$ gene (Genbank Accession number AB021221) or human HGF gene (Genbank Accession number M29145) (rAdLacZ, rAdVEGF, respectively) were constructed using commonly practiced molecular cloning techniques.

To construct the bacterial β-galactosidase expressing plasmid, a 3700 bp HindIII-BamHI β-galactosidase DNA fragment was inserted into pCA3 (Weisz et al, Circulation 2001, in press) under the control of a CMV promoter. A 600 bp BamHI DNA fragment containing the human $VEGF_{165}$ cDNA (gift of Dr. J. Abraham), including the secretion signal sequence was similarly inserted into pCA3.

The pCA3 plasmids containing either the $VEGF_{165}$ or the β galactosidase genes, were each co-transfected along with a pJM17 plasmid (Weisz et al, Circulation 2001, in press) into mammalian cells (Weisz et al, Circulation 2001, in press). Homologous recombination between the expression plasmid and pJM17 in these cells, replaced the E1 region and pBRX insert (Weisz et al, Circulation 2001, in press) with the expression cassette of the expression vectors. Virions were purified by $CsCl_2$ equilibrium concentration, dialyzed against 10 mM HEPES and, 1 mM EDTA, 10% glycerol and a viral titer was determined via mammalian cell infection (293 type cells).

The above described steps are also utilizable in the construction of an HGF expression vector, by using, for example, a PCR amplified cDNA fragment of human derived HGF mRNA.

Table 1 below lists various growth factors utilizable by the present invention and their corresponding GenBank accession numbers.

TABLE 1

| Growth Factor | GenBank accession number |
|---|---|
| $VEGF_{165}$ | AB021221 |
| PDGF | I01807 |
| HGF | M29145 |
| FGF1 | NM_000800 |
| FGF2 | M27968 |

VEGF Expression Analysis:

Total RNA was extracted from transformed tissues and subjected to PCR analysis in order to determine VEGF transcription in transformed cells.

RNA was extracted using a guanidinium thiocyanate extraction procedure, and a concentration thereof was calculated according to absorbance at 260 nm. Extracted RNA was used as a template for cDNA synthesis. A reverse transcription reaction was carried out in 50 µl of 1× reverse transcriptase (RT) buffer (Promega) including 0.5 mmol/L dNTPs, 20 U RNAsin (Promega), 100 pmol/L of a 3' anti sense primer (5'-TCCGGATCCTCACCGCCTCGGCT-TGTC-3', SEQ ID NO: 1), 1 µg of total RNA and 5 U avian myeloblastosis virus (AMV) reverse transcriptase (Promega). The reaction was carried out for 30 minutes at 37° C.; 60 minutes at 42° C. and 30 minutes at 52° C. followed by a denaturation step of 10 minutes at 94° C.

PCR amplification of resulting cDNA was performed in a 50 µl 1× reaction mixture containing 20 pmoles of a sense primer, 5'-GAAAGATCTCATATGGCTCCCATGGCA-GAAGGAGG-3' (SEQ ID NO: 2), 20 pmoles of the antisense primer (SEQ ID NO: 1), 240 µmole of dNTPs and 1 U of a Taq DNA Polymerase (Boehringer Mannheim). The PCR reaction was carried out as follows: 2 cycles of a denaturation step of 1 minute at 94° C., an annealing step of 5 minutes at 60° C. and an elongation step of 2 minutes at 72° C., followed by 36 cycles including a denaturation step of 40 seconds at 94° C., an annealing step of 1 minute at 60° C. and an elongation step of 1.5 minutes at 72° C. Resultant PCR products were electrophoresed in 1.2% agarose gel containing ethidium bromide and U.V. detectable bands were analyzed.

Western Blot Analysis:

Proteins extraction from liver tissues was performed by homogenizing samples of livers in homogenizing medium including 0.25M sucrose, 5 mM HEPES buffer, and 1 mM EDTA, pH 7.2 using Polytron type homogenizer. The protein content of each extracted sample was determined via spectrophotometry.

A heparin Sepharose column (Pharmacia) was used to isolate a VEGF protein fraction from the extracted samples. The VEGF containing fraction was separated in a discontinuous SDS polyacrylamide gel (6% stacking gel and 12.5% separating gel) under reducing conditions.

Following electrophoresis, the separated proteins were western blotted onto a nitrocellulose membrane (Schleicher and Schull). Nitrocellulose blots were blocked with 0.1% skim milk for 1 hour and incubated overnight with a polyclonal antibody raised against the amino terminal epitope (1-20 aa) of VEGF (Santa-Cruz) (diluted 1:700 in PBS containing 0.3% tween-20 and normal goat serum). Following primary antibody incubation, the blots were washed several times with PBS containing 0.3% tween-20 and incubated with a peroxidase conjugated secondary antibody (Sigma) for 1 hour. Following repeated washing as above, the western blots were incubated with ECL reagents (Sigma) and exposed to autoradiography. Densitometry was performed using 1 Kd software (Electrophoresis Documentation and Analysis System, EDAS 12-KODAK)

Example 2

Generation and Analysis of Model Animals Suffering from Liver Cirrhosis Cirrhosis Induction in Rats Carbon tetrachloride (CCl4) treatment was used to induce cirrhosis in Sprague-Dawley rats, which served as a first group of model animals. Twenty doses of CCl4 [50% (vol/vol) solution in mineral oil, 0.5 ml/kg body weight] were administered intra muscularly (i.m.) into the gluteal region every 5 days. A sodium phenobarbitone solution (500 mg/L in drinking water) was administered for 7 days prior to and during this CCl4 treatment (FIGS. 2a-3).

Liver tissue from the treated animal was excised and fixated in buffered formaldehyde (McLean E. K., et al, 1969; Proctor E. et al, 1982) and the presence and degree of cirrhosis in the liver tissue was determined by histopathological examination (FIGS. 4a-c).

Portal Vein Pressures Analysis:

Treated animals were anesthetized via i.m. administration of 30 mg/kg ketamine and 2 mg/kg xylazine. Following anesthesia, the abdominal cavity was entered via a midline incision and the superior mesenteric vein cannulated with a polyethylene catheter (FIG. 9). An i.v. bolus of 200 IU of heparin was administered, and the patency of the catheters was ensured with intermittent infusion of heparin-containing saline in small volumes. Portal vein pressures were measured using string gauge transducers, which were manually calibrated to a linear range of 0-60 mmHg and retested for accuracy following each measurement. The Pressure values were recorded via a physiograph device (Rajvanshi P. et al, 1996).

Liver Rat Vascular Bed Analysis Using Portovenography:

Portovenography was used in order to analyze the overall venous blood flow derived from the portal vein. A 21 gauge butterfly needle was inserted into the spleen of the treated animals, and radiocontrast-Omnipaque 350 (Sterling Pharmaceuticals Inc. Fa. Mueller, Hannover Germany) was administered at a flow rate of 4 ml/minute for 30 seconds using an autoinjector. Multiple images were digitally acquired at 2 frames/s using a clinical angiographer (Integris V 4000, Phillips Medical, Netherlands). Densitometry of the images was performed on control and VEGF-treated animals as previously described (Rajvanshi et al 1995; Rajvanshi et al, 1996).

Partial Hepatectomy:

Animals weighing 250-300 g were anesthetized via i.m. administration of 30 mg/kg ketamine and 2 mg/kg xylazine. A partial hepatectomy (⅔) was performed by entering into the abdominal cavity via a midline incision (Higgins et al. 1931).

Analysis of HGF and cMET mRNA Expression in Rat Liver:

RT-PCR analysis was performed in order to determine mRNA expression of HGF and cMET (an HGF-Receptor) in Rat liver.

Extracted liver RNA (1 mg) was reverse transcribed using MuLV reverse transcriptase and oligo d(T) as a primer.

The resulting first strands were PCR amplified with cMET and HGF specific primers. PCR amplification was performed as follows: 40 cycles including a denaturation step of 1 minute at 94° C., an annealing step of 1 minute at 60° C. and an elongation step of 1 minute at 72° C. A 1 Kb cDNA fragment of actin was PCR amplified in parallel to ensure specificity and integrity of the PCR reaction.

Resultant PCR products were electrophoresed in a 1.4% agarose gel containing ethidium bromide and their size determined according to co-migrated molecular weight markers.

In addition, the HGF and cMET PCR products were extracted from the gel, cloned into a pCR II vector (Invitrogen, San Diego, Calif.) and sequenced in order to confirm identity.

cMET specific primers: 5'-GAAAGATAAACCTCTCT-CATAATGAAGG-3' (SEQ ID NO: 3) and 5'-CACCACA-CAGTCAGGACACTG-3' (SEQ ID NO: 4) generated a PCR product approximately 555 bp long, extending from base pairs −20 to 535 of then cMET cDNA. HGF specific primers: 5'-ATCAGACACCACCGGCACAAAT-3' (SEQ ID NO: 5) and 5'-GAAATAGGGCAATAATCCCAAGGAA-3' (SEQ ID NO: 6) generated a PCR product approximately 700 bp long, extending from base pairs +710 to +1376 of the HGF cDNA.

Analysis of KDR mRNA Expression:

Northern analysis was performed on total RNA extracted from animal liver tissue in order to determine KDR mRNA expression. Total RNA (10-20 µg), was separated in a 1.2% formaldehyde-agarose gel and blotted onto a Nytrane membrane (MSI). A 791 bp fragment being capable of specifically hybridizing with the KDR gene was labeled with $^{32}$P via random priming methodology. Northern blot analysis was performed as previously described (Weisz et al, Circulation 2001, in press). Band intensity was determined and equilibrated according to the amount of RNA present in each band as calculated from the band intensity of the 18S band detected in the ethidium bromide stained gel.

Immunhistological Staining for Proliferating Cell Nuclear Antigen (PCNA):

Immunohistochemistry for proliferating cell nuclear antigen (PCNA) is performed using standard techniques (PCNA, 19 A2, Komulainen et al, *Environ Mol Mutagen* 2000; 36(4): 292-300).

Example 3

Transformed Cell Analysis

Effect of VEGF Gene Transfer on Endothelial Cell & Smooth Muscle Cell Proliferation HSVEC (Human saphenous vein endothelial cells, Weisz et al, Circulation 2001 in press) cells infected with the rAd-VEGF expression vector described hereinabove ($10^3$ pfu per cell) exhibited an increased cell proliferation rate as compared to rAdLacZ infected control cells and uninfected cell (FIG. 13a).

In contrast, rAdVEGF infection had no effect on the proliferation rate of HSVSMC (Human saphenous vein smooth muscle cells, Weisz et al, Circulation 2001) as compared to control cells (FIG. 13b).

Similar results were obtained using the BrdU nucleotide analog incorporation method (Weisz et al., IMAJ 2000). BrdU positive HSVEC and HSVSMC cells were counted five days following infection with the adenoviral vectors described above. Counting was effected using antibodies specific against the nucleotide analog. A significant increase in BrdU positive cells was detected in HSVEC cells following VEGF gene transfer (up to five fold as compared to control cells) while an increase was not observed in HSVSMC cells.

In addition to enhancing HSVEC proliferation, VEGF expression also induced morphological changes. Following VEGF expression the typical "cobblestone morphology" of HSVEC cells changed into capillary like structures typical of elongated endothelial cells.

In contrast no morphological changes were detected in HSVSMC cells expressing VEGF.

Transcription of VEGF messenger RNA was examined using RT-PCR analysis. VEGF transcription was detected five days following HSVEC infection with either rAdVEGFr which directs the transcription of a VEGF sense strand capable of being translated into the VEGF protein or rAd-VEGFw (control) which directs the transcription of an antisense strand of VEGF which is not translated In addition, infected cell supernatant was examined for VEGF protein levels at various time points following infection.

Analysis of VEGF transcription and translation levels has revealed that VEGF expression levels increase over time in infected cells.

Example 4

Generation and Analysis of a Second Group of Liver Cirrhosis Model Animals

Cirrhosis Induction in Rats:

A second group of liver cirrhosis model animals was generated. Thirty male Wistar rats weighing 350-400 g (n=80) were purchased from Jackson Laboratories or from a stock of animals at the Central Animal Facility of the Hanover Medical School. The animals were kept under 12:12 hour light and dark cycle and provided with standard laboratory feed and water. The animal experiments have been approved by the Bezirksregierung Hannover under the license number 509i-42502-99/203.

Liver cirrhosis was induced in 60 of these animals via an intraperitoneal injection of a CCl4 solution mixed with olive oil [50% (vol/vol) solution, 1 ml/kg body weight] performed twice a week for 10-16 weeks.

The rats generated by the above described procedure, were classified into fibrotic and cirrhotic groups according to liver specific enzyme activity (detected in sera, shown in FIGS. 10a-c) and according to histological features of the liver. Additionally, only animals having ascites (as detected via ultrasound) at any time throughout the CCl4/olive oil-treatment period were classified as having liver cirrhosis and thus were used for further analysis. Following ascites screening, 36 rats were selected for further research.

In Vivo Liver Transduction Using Recombinant Adenovirus:

Three groups of rats were used for adenovirus transduction as described hereinbelow. Ten untreated rats which served as control animals, ten rats having fibrotic livers according to predefined criteria (Knodell R G et al, Hepatology 1985; 1:431-5), and five rats having cirrhotic livers as determined above.

The animals were infected with 100 µl of the purified recombinant adenovirus Ad5.CMV-LacZ by intraportal injection. The infected rats were sacrificed 7 day post-infection, and the livers were fixed in 2% formaldehyde, 0.2% glutaraldehyde and 0.1% NP40 in PBS, pH 7.2 and subsequently frozen. The liver tissues were sliced into 10 µm sections using a cryostat. One liver lobe which was removed from each animal for detailed histological analysis was fixed in buffered 4% formalin, embedded in paraffin, cut into 5 µm sections and stained with hematoxylin/eosin (AFIP, Manual of Histologic Methods, McGraw Hill Book Co., 1968) and with elastica/von-Giesson (AFIP, Manual of Histologic Methods, McGraw Hill Book Co., 1968) for conventional histological evaluation (FIGS. 4a-c).

Histological Evaluation of Rat Liver:

Classification of the liver derived tissues into fibrotic or cirrhotic tissue was performed according to criteria of the Knodell index (Knodell R G et al, Hepatology 1985;1:431-5). Fibrotic livers were characterized by fibrous portal expansion and/or bridging fibrosis (portal-portal or portal central linkage), while cirrhotic livers were characterized by complete architectural disorganization with a micro-nodular pattern and large amounts of fibers lining the hepatic nodules.

β-galactosidase Histochemical Analysis:

Tissue sections of rat livers and hepatocyte cell cultures (FIGS. 5a-8c) were each transduced with the Ad5.CMV-LacZ expression vector described hereinabove. Expression analysis of β-galactosidase enzyme in the cell cultures and tissue sections was carried out using the β-gal Staining Kit according the manufacturers protocol (Boehringer Mannheim, Germany). Briefly, the cell cultures or fixed tissue sections were rinsed three times with phosphate buffered saline (PBS), pH 7.2, and incubated in a reaction mixture containing 5 mM K3Fe(CN)6, 2 mM MgCl2 and 1 mg/ml X-gal solution (5-bromo-4-chloro-3-indoyl-(-D-galactopyranoside) in PBS, pH 7.2, for 2 h at 37° C.

Serum Enzymes:

The activity levels of several serum enzymes were determined at the time of viral transduction (injection) or at the time of blood pressure measurement. Enzymes activities were measured using a Hitachi Automatic Analyzer (Boehringer Mannheim, Germany) following standard procedures (reagents from Boehringer Mannheim, Germany). The enzymes tested included aspartate aminotransferase (AST), alanine aminotransferase (ALT) and cholinesterase (CHE).

Portal Vein Pressures Analysis:

Portal vein pressure was measured in a cannulated (polyethylene 50 tubing) and ligated portal vein. A portal vein catheter, which was connected to quartz transducers, was used to obtain pressure readings, which were registered, using a multichannel recorder (FIG. 9).

Example 5

β-galactosidase Activity in Transduced Liver Tissue Sections:

β-galactosidase activity was detected via X-gal staining performed according to the manufacturers protocol. Positive blue cells as well as negative cells were counted in cryostat sections under the microscope. FIG. 12 is a graph illustrating the percentage of blue cells expressing β-galactosidase in normal, fibrotic and cirrhotic liver specimens. FIGS. 6a-8c show microphotographs from respective cryostat sections. As can be seen in these Figures, intraportal injection of $0.5 \times 10^9$ pfu Ad5.CMV-LacZ resulted in a 48.8%±7% transduction rate of the liver (n=10) in normal animals. In fibrotic liver tissue the transduction rate with an equivalent amount of virus was reduced to a mean level of 23.1±5%. A further but still significant reduction of the transduction efficacy was noted in cirrhotic rats (7±2%). Virus transduced cells were distributed throughout the normal and fibrotic liver lobes analyzed, while in the cirrhotic liver, transduced cells were observed mainly around the periportal area and along the septa.

Serum Enzymes Activity:

The activity levels of aspartate aminotransferase (AST/GOT), alanine aminotransferase (GPT/ALT) and cholinesterase (CHE) were measured for normal, fibrotic and cirrhotic rats (FIGS. 10a-c respectively). In the cirrhotic animals CHE-levels (0.97±0.46 kU/ml) were significantly reduced as compared to the normal (2.8±0.7 kU/ml) as well as to the fibrotic rats (2.6±0.6 kU/ml).

Portal Vein Pressures Analysis:

Portal blood pressure was measured in all animals used in the experiments. Polyethylene tubing was placed into the portal vein accessed via midline laparotomy performed under general anesthesia. The tubing was connected to the transducers as described hereinabove and used to measure portal vein pressures.

As shown in FIG. 11a, mean portal pressures in normal rats injected with 100 μl NaCl 0.9% and 100 μl $0.5 \times 10^9$ pfu Ad5.CMV-LacZ adenovirus were 4.7±1.7 mmHg and 4.4±1.2 mmHg, respectively. In animals having liver fibrosis, the mean portal pressures recorded were 9.4±2.9 mmHg following injection with 100 μl NaCl 0.9% and 8.9±1.8 mmHg following injection with 100 μl $0.5 \times 10^9$ pfu Ad5.CMV-LacZ adenovirus (FIG. 11b). The mean portal blood pressure recorded in cirrhotic rats was 19.6 mmHg±7.4 mm Hg seven days following injection of 100 μl NaCl 0.9%, while 7 days following injection with $0.5 \times 10^9$ pfu Ad5.CMVLacZ the mean portal blood pressure was marginally and non-significantly reduced to 17.2±5.4 mmHg (FIG. 11c).

Example 6

Expression of HGF in SMCs and ECs

Generation of Recombinant Adenoviral Vectors Encoding HGF Gene Alone or HGF and GFP Genes:

The recombinant adenoviral vector expressing the human HGF gene was constructed by a modified AdEasy protocol as described in Vogelstein B. PNAS 1998. A 2300 bp Bam HI-Sal I fragment including HGF cDNA (nucleotide coordinates 102-2288 of GenBank Accession number M29145 ) was ligated into the BglII-Sal I site of the pAdShuttle-CMV vector under the control of the CMV promoter. The recombinant adenoviral vector expressing the human HGF and GFP genes was also constructed using a modified AdEasy protocol. A 3700 bp Bam HI fragment of HGF-IRES-GFP cDNA (obtained from the LXSN HGF IRES GFP plasmid) was ligated into the BglII site of the pAdShuttle-CMV vector under the control of the CMV promoter. The shuttle vectors were linearized by PmeI digestion and purified by Qiaquick gel extraction kit (Qiagen, USA). The linearized shuttle vector and pAdEasy-1 were co-transformed into competent BJ5183 cells using electroporation. Positive clones containing the recombinant adenoviral vectors were selected according to PCR and restriction map analysis. The recombinant adenoviral plasmids were linearized by PacI digestion, purified and transfected into 293 cells using Lipofectamine 2000 (Gibco BRL, USA). Seven days post transfection, cytopathological effect (CPE) occurred and 100% of the cells expressed GFP. The cells were harvested and viral extracts were further amplified in 293 cells. The viral stock titer was determined by serial dilution assay in 293 cells and ranged $\sim 10^{11}$ pfu/ml. The expression of the transgene was confirmed by western analysis of the infected cells condition media.

Construction of Retroviral Vectors for Expression of HGF or Co-Expression of HGF and EGFP Recombinant retroviral vector LXSN-HGF encoding the human HGF gene was constructed by inserting the human HGF cDNA 2300 bp BamH1 fragment (nucleotide coordinates 102-2288 of GenBank Accession number M29145) into the BamHI site of plasmid pLXSN (# K1060-B Clontech, USA) under the control of Mo-MULV 5' long terminal repeat (LTR).

A bicistronic recombinant retroviral vector encoding both the HGF and EGFP genes was subcloned into plasmid pLXSN as follows. First, a 1400 bp IRES-EGFP EcoRI-HpaI fragment excised from pIRES2-EGFP (Clontech, cat#6029-1) was inserted into EcoRI-HpaI-digested pLXSN for construction of the plasmid pLXSN-IRES-EGFP. In a second step, the human HGF Xho1-Sal1 fragment (2300 bp) was cloned into the Sal1 site of pLXSN-IRES-EGFP; expression of HGF and EGFP in the resultant construct is regulated by Mo-MULV 5' long terminal repeat (LTR).

Generation of Pseudotyped Recombinant Retroviral Vectors Encoding HGF

The pLXSN-HGF-EGFP or the pLXSN-HGF vectors were transfected into 293FLYA packaging cells using Lipofectamine (Gibco BRL, USA). Forty eight hours post transfection, a supernatant from confluent cultures of viral producer cells was collected, filtered (0.45 µm) and added to 293 FLYGALV packaging cells. Transduced cells were grown under G418 selection (400 µg/ml) and individual colonies were collected and screened for EGFP expression, using an inverted fluorescent microscope, and HGF expression by Western analysis of transduced cell-conditioned medium. The viral titer of each colony was determined via transduction of TE671 cells and titers of ~$10^6$ ffu/ml were established. The colonies with the highest-titers were selected, and fresh supernatant fractions were collected for transduction of EC and SMC cell cultures.

Verifying Transgene Expression following Gene Transfer

Cell Culture:

Endothelial cells (EC) were isolated from human saphenous veins (HSVEC), and cultured on gelatin-coated dishes in M20 containing M-199 Medium (Biological Industries, Israel) supplemented with 20% FCS, 2mM L-Glutamin, 100 units/ml penicillin, and 0.1 mg/ml streptomycin, 100 µg/ml Heparin (Sigma) and 2 ng/ml bFGF (Enco). Human ECs were identified via immunohistochemistry analysis using anti Von-Willebrand factor specific antibodies (Zymed, USA). Smooth muscle cells (SMC) were cultured by explant outgrowth from human saphenous veins (HSVSMC) and left internal mammary arteries (HLSMC). Cells were cultured in Dulbeco's Modified Eagles Medium (DMEM) (Biological Industries, Israel) supplemented with 10% human serum, 2 mM L-Glutamin, 100 units/ml penicillin, 0.1 mg/ml streptomycin and 2 ng/ml bFGF. SMCs were identified by immunohistochemistry analysis using specific anti-α smooth muscle actin antibodies (Zymed, USA).

The packaging cell lines 293-FLYA, 293-FLY10A, 293-FLYGALV and TEFLYGA (obtained from Dr F. L. Cosset-Lion, France) were grown in DMEM supplemented with 10% FCS, 2 mM L-Glutamin, 100 units/ml penicillin, 0.1 mg/ml streptomycin, 6 µg/ml blasticidin and 6 µg/ml phleomicin. The packaging cell lines PA317, 293E3 (obtained from Dr. J. Exelrod, Hadassa, Jerusalem) were grown in DMEM supplemented with 10% FCS, 2 mM L-Glutamin, 100 units/ml penicillin, and 0.1 mg/ml streptomycin.

Infection of EC and SMC with Recombinant Adenovirus Vectors

EC and SMC cells were seeded at 70% confluence on fibronectin pre-coated plates (4.5 µg/ml) 20 hours prior to infection and grown in complete medium (M20). At the day of infection, the medium was replaced with fresh M199 (without serum) and the recombinant virus was added at a Multiplicity of Infection of 3000 (MOI=3000, i.e., 3000 viral particles per cell). The cells were subjected to a gentle tilt every 20 minutes over a 90 minutes incubation period. Following infection, the virus-containing medium was replaced with complete medium (M20). The infection rate was detected by visualization of GFP expression (FIGS. 14a-d) using a fluorescent inverted microscope (TE200 Nikon, Japan) through fluorescent GFP filter (GFP-LP, Nikon).

Transduction of EC and SMC with Recombinant Retroviral Vectors

EC cells (passage 4-9) were seeded (105 cells per 35-mm well) in fibronectin-coated plates (4.5 µg/ml) and grown in complete medium for 24 hours. One hour prior to transduction, the medium was replaced with serum free M199 containing 0.1 mg/ml of the cationic polymer DEAE-dextran (Sigma). Following pre-conditioning, the cells were washed three times with phosphate-buffered saline (PBS). Transduction was performed by incubating the cells for 4 hours with supernatant containing viruses which was collected and filtered (0.45µ) from the virus producing packaging cell lines. At the end of the incubation the medium was replaced with fresh M20 medium. Successful HGF gene transfer is indicated by the green fluorescence as demonstrated in FIG. 15. Note the high transduction rate with the pseudotyped retroviral vectors.

HGF Over-Expression by Infected EC and SMC

Western Blot Analysis:

HGF protein expression by adenoviral or retroviral infected EC and SMC was detected by western blot analysis of the conditioned medium. Twenty four hours post infection, the medium was replaced with a serum free medium and cells were grown for additional 48 hours. Samples of the conditioned medium (30 µl) were separated on 8% SDS polyacrylamide gel under reducing conditions, and electrotransferred onto nitrocellulose membrane (Shleicher & Schull). The blots were blocked with 0.1% skim milk in TBS containing 0.3% Tween-20 (TBST) for 1 hour at room temperature using gentle agitation. The blots were incubated with primary antibody diluted in blocking solution for 2 hours at room temperature. 1:1000 dilution of polyclonal goat biotinylated anti-HGF antibody (#BAF294, R@D Systems, Inc., USA) was used for HGF detection. Following primary antibody incubation, the blots were washed three times with TBST and incubated with anti-goat peroxidase-conjugate antibody (Sigma) diluted 1:10000 in TBST for 1 hour at room temperature. Following three washes with TBST, the bound secondary antibody was visualized using an ECL protocol (Sigma). HGF expression in the infected cells is illustrated in FIG. 16. Bands which correspond to α and β HGF are clearly more visible in the EC fractions. This is due to the fact that ECs exhibit more efficient processing of pro-HGF to its more active forms. Similar results were obtained using the retroviral vector transduced cells (FIG. 17).

Physiological Effects of HGF Gene Transfer

Proliferation Assay:

EC cells (passages 5-11) were infected with rAdHGF-GFP or rAdGFP; non-infected cells served as a control. Serum-containing medium was added to the cells following a 90 minutes exposure to adenoviral vectors at 37° C. Twenty-four hours post infection, the cells were seeded at 30% confluence (1×10⁴ cells/well) in 24 wells plate pre-coated with fibronectin (4.5 μg/ml) and supplemented with M199 containing 2% human serum. The assay was performed in triplicates. Proliferation rate was detected 2 and 4 days after infection using cell coulter cell counting.

Scatter Assay:

Madin Darby canine kidney (MDCK) cells were used to verify the biological activity of HGF in scatter assay. MDCK cells were seeded in 96-well plate at the concentration 3000 cells per well. The condition medium from 293 Adeno HGF/GFP producing cells or 293 FLY GALV retro HGF/GFP producing cells was centrifuged to collect the cells and the supernatant diluted in 100 μl of DMEM, 5% FCS was added to the cells. Following an overnight incubation, the cells were fixed in 4% PFA, stained in H&E, and visualized using an inverted light microscope (FIGS. 18a-d). The same scattering effect on MDCK cells was shown when supernatant fractions were collected from cells transduced by retroviral-HGF vectors (FIGS. 19a-b).

Phosphorylation of cMET Receptor:

MDCK and SMC were seeded in 60 mm plates at ~90% confluence and grown in serum free media supplemented with 5 μg/ml Transferrin and 5 μg/ml Insulin for 24 hrs. The cells were incubated for 15 minutes at 37° C. and in the presence of 30 μl of the conditioned medium of 293 rAdHGF-GFP or rAdGFP producing cells diluted in binding buffer (DMEM containing 20 mM HEPES, pH 7.2 and 0.2% gelatin). Recombinant human HGF diluted in binding buffer (to a concentration of 30 ng/ml) was used as a positive control. Following incubation, the cells were washed with cold PBS containing 100 μM Na3VO4 and lysed with lysis buffer containing 20 Mm Tris-HCl pH-7.5, 150 Mm NaCl, 1% Triton X-100,10% glycerol, 1 mM PMSF, 2 μg/ml Leupeptine, 2 μg/ml Aprotinine, and 100 μM Na3VO4. The lysates were cleared by centrifugation, and protein content was measured using BioRad protein assay according to the manufacturer's instructions. Equal amounts of protein from the different lysates were recovered for immunoprecipitation. The lysates were incubated overnight at 40° C. with protein-A sepharose conjugated anti-phosphotyrosine antibodies PY99 (Santa-Cruz, USA). The beads were subsequently washed 4 times with cold PBS, an SDS/PAGE sample buffer was then added to the beads and the beads were boiled for 3 minutes. The recovered supernatant was separated on an SDS/PAGE gel and transferred onto a membrane as described above. The resultant Western blot, which is shown in FIGS. 20a-b was immunoprobed with anti-cMET antibodies (R@D Systems, Inc., USA). Phosphorylation of the cMET receptor clearly demonstrates biological activity for the HGF expressed by the genetically modified cells of the present invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES

Additional References Cited Herein

1. Podolsky D K, Isselbacher K J. Cirrhosis and alcoholic liver disease. In Harrison's principles of internal medicine. Eds Fauci A S, et al. McGraw-Hill, New York. 1998, 1704-1717.
2. Sherlock S, Dooley J. in Diseases of the liver and biliary system. Blackwell Sciences Ltd. London. 1997, 371-384.
3. Villanueva C, Balanzo J, Novella M T, et at. Nadolol plus isosorbide mononitrate compared with sclerotherapy for the prevention of variceal rebleeding. N Engl J Med 1996; 334:1624-9.
4. Schmidt H H, Tietge U J, Manns M P: Perspectives of liver cell transplantation: a review. Hepatogastroenterology. 1997; 44:1013-8.
5. Lieber A, Vrancken Peeters M, Meuse L, Fausto N, Perkins J, Kay M A. Adenoviral-mediated urokinase gene transfer induces liver regeneration and allows for efficient retrovirus transduction of hepatocytes in vivo. Proc Natl Acad Sci USA 1995;92:6210-6214.
6. Yamane A., Seetharam L., Yamaguchi S., Gotoh N., Takahashi T., Neufeld G., Shibuya M. A new communication system between hepatocytes and sinusoidal endothelial cells in liver through vascular endothelial growth factor and Flt tyrosine Chinese receptor family (Flt-1 and KDR/Flks-1). Oncogen 1994; 9:2683-2690.
7. Monacci W. T., Merrill M. J., Oldfield E. H. Expression of vascular permeability factor/vascular endothelial growth factor in normal rat tissues. Am J Cell Physiol 1993; 264 (Cell Physiol 33):C995-C1002.
8. Leung D W, Cachianes G, Kuang W J, Goeddel D V, Ferrara N. Vascular endothelial growth factor is a secreted angiogenic mitogen. Science. 1989; 246: 1306-9.
9. Jakeman L B, Winer J, Bennett G L, Altar C A, Ferrara N. Binding sites for vascular endothelial growth factor are localized on endothelial cells in adult rat tissues. J-Clin-Invest 1992; 89:244-53.
10. Hanahan D. Signaling vascular morphogenesis and maintenance. Science 1997; 277:48-50.
11. Mochida S., Ishikawa K., Inao M., Shibuya M., Fujiwara K. Increased expressions of vascular endothelial growth factor and its receptors, flt-1 and KDR/flk-1, in regenerating rat liver. Biochem Biophys Res Comm 1996; 226:176-179.
12. Mochida S, Ishikawa K, Toshima K, et al. The mechanism of hepatic sinusoidal endothelial cell regeneration: a possible communication system associated with vascular endothelial growth factor in liver cells. J Gastroenterol Hepatol 1998; 13:S 1-5.
13. Bunchet E., Fujieda K. Capillarization and venuralization of hepatic sinusoids in porcine serum-induced rat liver fibrosis: a mechanism to maintain liver blood flow. Hepatology 1993; 18:1450-1458.
14. Noji S, Tashiro K, Koyama E, et al. Expression of hepatocyte growth factor gene in endothelial and Kupffer cells of damaged rat livers, as revealed by in situ hybridization. Biochem Biophys Res Commun 1990; 173:42-7.s 15. Akiyoshi F, Sata M, Suzuki H, et al. Serum vascular endothelial growth factor levels in various liver diseases. Digestive Diseases and Sciences 1998; 43:41-45.
16. Cao Y, O'Reilly M S, Marshall B, Flynn E, Ji R W, Folkman J. Expression of angiostatin cDNA in a murine fibrosarcoma suppresses primary tumor growth and produces long-term dormancy of metastases. J-Clin-Invest. 1998; 101:1055-63.
17. Carmeliet P, Ferreira V, Breier G, Pollefeyt S, Kieckens L, Gertsenstein M, Fahrig M, Vandenhoeck A, Harpal K, Eberhardt C, Declercq C, Pawling J, Moons L, Collen D, Risau W, Nagy A. Abnormal blood vessel development and
18. lethality in embryos lacking a single VEGF allele. Nature 1996; 380:435-9.
19. Anderson W F. Human gene therapy. Nature 1998;392: 25-30.
20. Lewis B S, Flugelman M Y, Weisz A, Keren-Tal I, Schaper W. Angiogenesis by gene therapy. Cardiovascular Research 1997; 35:490-7.
21. Mulligan R C. The basic science of gene therapy. Science 1993; 260:926-32.
22. Flokman J. Therapeutic angiogenesis. Circulation 1998; 97:1108-1110.
23. Ilan Y, Sauter B, Chowdhury N R, Reddy B V, Thummala N R, Droguett G, Davidson A., Ott M, Horwitz M S, Roy Chowdhury J R. Oral tolerization to adenoviral proteins permits repeated adenovirus-mediated gene therapy in rats with pre-existing immunity to adenovirus. Hepatology 1998; 27:1368-76
24. Banai S, Shweiki D, Pinson A, Chandra M, Lazarovici G, Keshet E. Upregulation of vascular endothelial growth factor expression induced by myocardial ischaemia: implications for coronary angiogenesis. Cardiovascular Research 1994; 28:1176-1179.
25. Waltenberger J, Mayr U, Pentz S, Hombach V. Functional upregulation of the vascular endothelial growth factor receptor KDR by hypoxia. Circulation 1996; 94:1647-1654.
26. Yamaguchi R, Yano H, Iemura A, Ogasawara S, Haramaki M, Kojiro M. expression of vascular endothelial growth factor in human hepatocellular carcinoma. Hepathology 1998; 28:68-77.
27. McLean E. K., McLean A. E. M., Sutton P. M. Instant cirrhosis—an improved method for producing cirrhosis of the liver in rats by simultaneous administration of carbon tetrachloride and phenobarbitone. Br J Exp. Pathol 1969; 50:502-506.
28. Proctor E., Chatamra K. High yield micronodular cirrhosis in the rat. Gastroenterology 1982; 82:1183-1190.
29. Rajvanshi P., Kerr A., Bhargava K. K., Burk R. D., Gupta S. Efficacy and safety of repeated hepatocyte transplantation for significant liver repopulation in rodents. Gastroenterology 1996; 111:1092-1102.
30. Rajvanshi P., Kerr A., Bhargava K. K., Burk R. D., Gupta S. Studies of liver repopulation using the dipeptidyl peptidase IV deficient rat and other rodent recipients: cell size and structure relationships regulate capacity for increased transplanted hepatocyte mass in the liver lobe. Hepatology 1995; 23:482-496.
31. Higgins G. M., Anderson R. M. Experimental pathology of the liver, I: restoration of the liver of the white rat following partial surgical removal. Arch Pathol 1931; 12:186-202.
32. Weisz A, Koren B, Fischer L, Lewis B S, Flugelman M Y. Therapeutic angiogenesis for ischemic syndromes. Isr Med Assoc J. 2000; 2 Suppl:52-7.

What is claimed is:

1. An isolated population of cells comprising a hepatocyte genetically transformed to express VEGF and an endothelial cell genetically transformed to express HGF.

2. The isolated population of cells of claim 1, wherein the population of cells is stably or transiently transformed.

3. The isolated population of cells of claim 1, wherein said endothelial cell is isolated from a source selected from the group consisting of venous tissue, arterial tissue, fat tissue, progenitor cells, circulating endothelial cells and bone marrow stem cells.

4. The isolated population of cells of claim 1, wherein expression of said VEGF and HGF is independently regulatable.

5. A method of inducing liver regeneration in a damaged liver tissue region of an individual, the method comprising the step of administering to the damaged liver tissue region of the individual endothelial cells genetically transformed to express HGF and hepatocytes genetically transformed to express VEGF, thereby inducing liver regeneration in the damaged liver tissue region of the individual.

6. The method of claim 5, wherein the method is utilized for treating or alleviating liver damage in an individual.

7. The method of claim 5, wherein said individual is a human being.

8. The method of claim 5, wherein said endothelial cells and/or said hepatocytes are isolated from the individual.

* * * * *

```
                          SEQUENCE LISTING

<160> NUMBER OF SEQ ID NOS: 6

<210> SEQ ID NO 1
<211> LENGTH: 27
<212> TYPE: DNA
<213> ORGANISM: Artificial
<220> FEATURE:
<223> OTHER INFORMATION: synthetic oligonucleotide

<400> SEQUENCE: 1
tccggatcct caccgcctcg gcttgtc                                           27

<210> SEQ ID NO 2
<211> LENGTH: 35
<212> TYPE: DNA
<213> ORGANISM: Artificial
<220> FEATURE:
<223> OTHER INFORMATION: synthetic oligonucleotide

<400> SEQUENCE: 2
gaaagatctc atatggctcc catggcagaa ggagg                                  35

<210> SEQ ID NO 3
<211> LENGTH: 28
<212> TYPE: DNA
<213> ORGANISM: Artificial
<220> FEATURE:
<223> OTHER INFORMATION: synthetic oligonucleotide
```

```
<400> SEQUENCE: 3
gaaagataaa cctctctcat aatgaagg                                              28

<210> SEQ ID NO 4
<211> LENGTH: 21
<212> TYPE: DNA
<213> ORGANISM: Artificial
<220> FEATURE:
<223> OTHER INFORMATION: synthetic oligonucleotide

<400> SEQUENCE: 4
caccacacag tcaggacact g                                                     21

<210> SEQ ID NO 5
<211> LENGTH: 22
<212> TYPE: DNA
<213> ORGANISM: Artificial
<220> FEATURE:
<223> OTHER INFORMATION: synthetic oligonucleotide

<400> SEQUENCE: 5
atcagacacc accggcacaa at                                                    22

<210> SEQ ID NO 6
<211> LENGTH: 25
<212> TYPE: DNA
<213> ORGANISM: Artificial
<220> FEATURE:
<223> OTHER INFORMATION: synthetic oligonucleotide

<400> SEQUENCE: 6
gaaatagggc aataatccca aggaa                                                 25
```